(12) United States Patent
Popplewell

(10) Patent No.: US 7,419,659 B2
(45) Date of Patent: Sep. 2, 2008

(54) EXPRESSION CONTROL USING VARIABLE INTERGENIC SEQUENCES

(75) Inventor: Andrew George Popplewell, Slough (GB)

(73) Assignee: UCB Pharma S.A. (BE)

(*) Notice: Subject to any disclaimer, the term of this patent is extended or adjusted under 35 U.S.C. 154(b) by 227 days.

(21) Appl. No.: 10/498,273

(22) PCT Filed: Dec. 5, 2002

(86) PCT No.: PCT/GB02/05466

§ 371 (c)(1),
(2), (4) Date: Nov. 17, 2004

(87) PCT Pub. No.: WO03/048208

PCT Pub. Date: Jun. 12, 2003

(65) Prior Publication Data

US 2006/0104949 A1 May 18, 2006

(30) Foreign Application Priority Data

Dec. 5, 2001 (GB) ................................. 0129105.3

(51) Int. Cl.
*A61K 48/00* (2006.01)
*C12P 21/04* (2006.01)
*C12N 15/00* (2006.01)
*C07H 21/04* (2006.01)

(52) U.S. Cl. .................. 424/93.2; 435/69.6; 435/320.1; 536/23.53; 536/24.1

(58) Field of Classification Search ................ 424/93.2; 435/69.6, 320.1; 536/23.53, 24.1
See application file for complete search history.

(56) References Cited

U.S. PATENT DOCUMENTS

| 3,927,193 | A | | 12/1975 | Hansen et al. |
| 4,331,647 | A | | 5/1982 | Goldenberg |
| 4,348,376 | A | | 9/1982 | Goldenberg |
| 4,361,544 | A | | 11/1982 | Goldenberg |
| 4,444,744 | A | | 4/1984 | Goldenberg |
| 4,460,561 | A | | 7/1984 | Goldenberg |
| 5,698,435 | A | * | 12/1997 | Robinson et al. ............ 435/328 |
| 7,018,809 | B1 | * | 3/2006 | Carter ....................... 435/69.1 |
| 2005/0042219 | A1 | * | 2/2005 | Woulfe et al. ............. 424/145.1 |
| 2005/0181448 | A1 | * | 8/2005 | Popplewell et al. .......... 435/7.1 |

FOREIGN PATENT DOCUMENTS

| EP | 0 120 694 A2 | | 10/1984 |
| EP | 0 125 023 A1 | | 11/1984 |
| EP | 0 171 496 A2 | | 2/1986 |
| EP | 0 173 494 A2 | | 3/1986 |
| EP | 0 239 400 A2 | | 9/1987 |
| GB | 0124317.9 | * | 10/2001 |
| WO | WO 86/01533 | | 3/1986 |
| WO | WO 90/07861 | | 7/1990 |
| WO | WO 91/09967 | | 7/1991 |
| WO | WO 95/01155 | | 1/1995 |
| WO | WO 01/94585 | * | 6/2001 |
| WO | 01/94585 | | 12/2001 |

OTHER PUBLICATIONS

Muller et al. (FEBS Letters 422:259-264 (1998).*
Cheung et al. (J. Virology 66(11):6714-6720 (1992).*
Sequence search alignment for SEQ ID Nos. 4, 7, 10 and 13 (pp. 1-4).*
Adhin, M.R. and van Duin, J., "Scanning Model for Translational Reinitiation in Eubacteria," *J. Mol. Biol.*, 213:811-818, (1990).
Andre, A., et al., "Reinitiation of protein synthesis in *Escherichia coli* can be induced by mRNA *cis*-elements unrelated to canonical translation initiation signals," *FEBS Letters*, 468:73-78, (2000).
Begent, R. H. J., et al., "A Serum Factor With Potential As A Tumour Marker In Malignant Lymphoma," *Br. J. Cancer*, 41:481-484, (1980).
Better, M., et al., "*Escherichia coli* Secretion of an Active Chimeric Antibody Fragment," *Science*, 240:1041-1043, (May 20, 1988).
Knappik, A. and Plückthun, A., "Engineered turns of a recombinant antibody improve its in vivo folding," *Protein Engineering*, 8(1):81-89, (1995).
Köhler, G. and Milstein, C., "Continuous cultures of fused cells secreting antibody of predefined specificity," *Nature*, 256:495-497, (Aug. 7, 1975).
Koppel, G.A., "Recent Advances with Monoclonal Antibody Drug Targeting for the Treatment of Human Cancer," *Bioconjugate Chem.*, 1:13-23, (1990).
Makrides, S.C., "Strategies for Achieving High-Level Expression of Genes in *Escherichia coli*," *Microbiological Reviews*, 60(3):512-538, (Sep. 1996).
Oeltmann, T.N. and Frankel, A.E., "Advances in immunotoxins," *FASEB J.*, 5:2334-2338, (1991).
Riechmann, L., et al., "Reshaping human antibodies for therapy," *Nature*, 332:323-327, (Mar. 24, 1988).
Simmons, L.C. and Yansura, D.G., "Translational level is a critical factor for the secretion of heterologous proteins," *Nature Biotechnology*, 14:629-634, (May 1996).
Spanjaard, R.A. and van Duin, J., "Translational reinitiation in the presence and absence of a Shine and Dalgarno sequence," *Nucleic Acids Research*, 17(14):5501-5507, (1989).
van den Bergh, H., "Light and porphyrins in cancer therapy," *Chemistry in Britain*, pp. 430-439, (May 1986).
Vaughan, T.J., et al., "Human antibodies by design," *Nature Biotechnology*, 16:535-539, (1998).
Waldman, T.A., "Monoclonal Antibodies in Diagnosis and Therapy," *Science*, 252:1657-1662, (Jun. 21, 1991).
Published PCT International Search Report dated Jun. 12, 2003 for International Application No. PCT/GB2002/005466, International Filing Date: Dec. 5, 2002.

* cited by examiner

*Primary Examiner*—Larry Helms
*Assistant Examiner*—Lynn Bristol
(74) *Attorney, Agent, or Firm*—Cozen O'Connor

(57) ABSTRACT

The present invention relates to a method of production of antibodies wherein the heavy and light chains of a particular antibody molecule are encoded by the DNA present in a dicistronic message in which the two cistrons are linked by an optimised intergenic sequence.

6 Claims, 19 Drawing Sheets

Fig. 2

Sequence of OmpA Oligonucleotide Adapter

Figure 1:
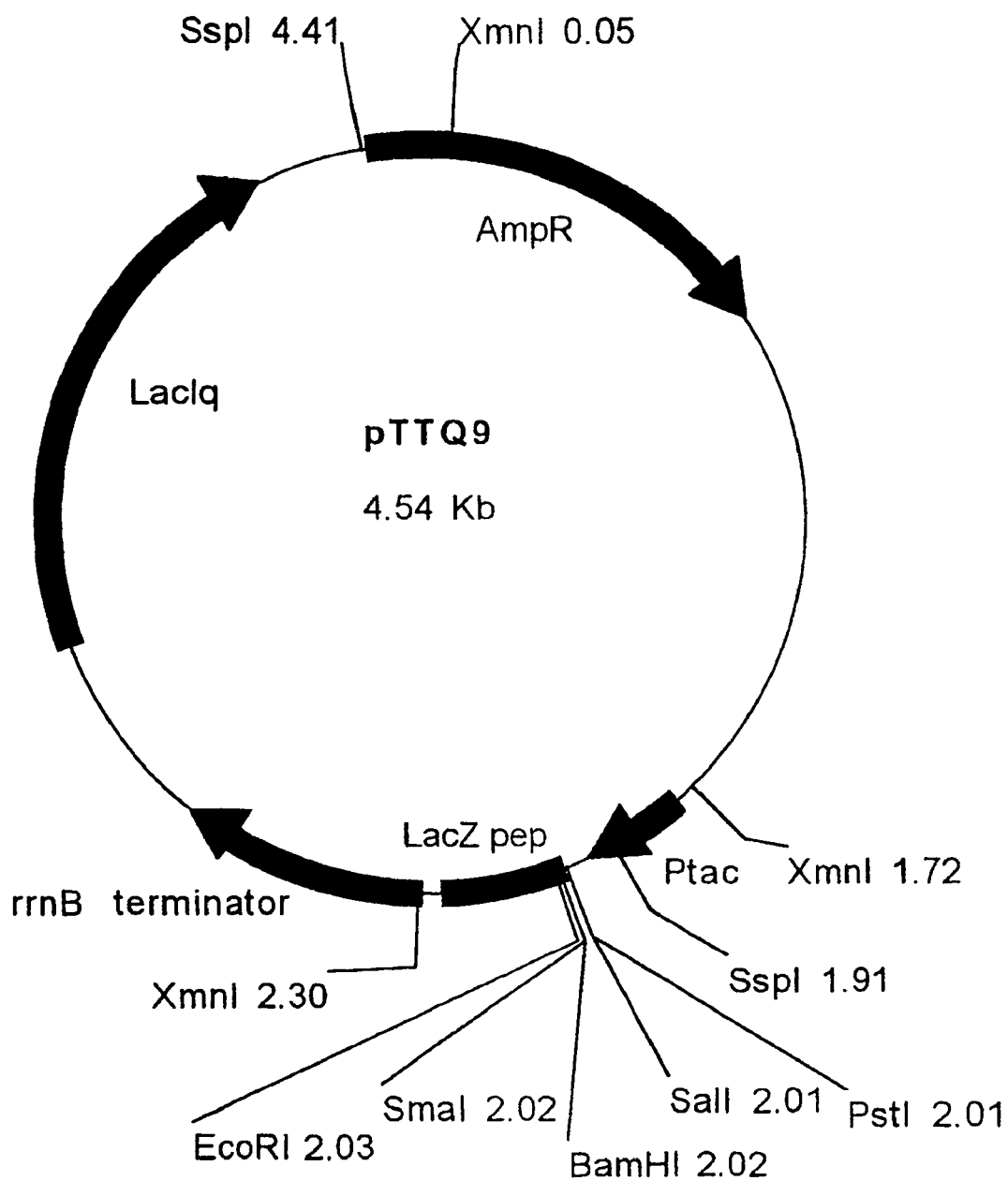

```
                                                    OmpA Leader
                                                   ┌─────────▶

10             20             30             40
          *              *              *              *
  XhoI         XbaI           S.D.
  T CGA  GTT  CTA  GAT  AAC  GAG  GCG  TAA  AAA  ATG  AAA  AAG  ACA
         CAA  GAT  CTA  TTG  CTC  CGC  ATT  TTT  TAC  TTT  TTC  TGT
                                                  M    K    K    T>

50             60             70             80
          *              *              *              *
              MunI           StyI           SplI
  GCT  ATC  GCA  ATT  GCA  GTG  GCC  TTG  GCT  CTG  ACG  TAC  GAG  TCA
  CGA  TAG  CGT  TAA  CGT  CAC  CGG  AAC  CGA  GAC  TGC  ATG  CTC  AGT
   A    I    A    I    A    V    A    L    A
         90
          *
    EcoRI
  GG
  CCT  TAA
```

- Internal restriction sites are shown in bold
- The 5' XhoI cohesive end ligates into the vector SalI site, blocking it
- S.D. represents the OmpA Shine Dalgarno sequence

Fig. 5
Nucleotide sequence of pTTO-1

```
         10         20         30         40         50         60         70
AATTCTCATG TTTGACAGCT TATCATCGAC TGCACGGTGC ACCAATGCTT CTGGCGTCAG GCAGCCATCG
TTAAGAGTAC AAACTGTCGA ATAGTAGCTG ACGTGCCACG TGGTTACGAA GACCGCAGTC CGTCGGTAGC 80         90        100        110        120        130        140
GAAGCTGTGG TATGGCTGTG CAGGTCGTAA ATCACTGCAT AATTCGTGTC GCTCAAGGCG CACTCCCGTT
CTTCGACACC ATACCGACAC GTCCAGCATT TAGTGACGTA TTAAGCACAG CGAGTTCCGC GTGAGGGCAA 150        160        170        180        190        200        210
CTGGATAATG TTTTTTGCGC CGACATCATA ACGGTTCTGG CAAATATTCT GAAATGAGCT GTTGACAATT
GACCTATTAC AAAAAACGCG GCTGTAGTAT TGCCAAGACC GTTTATAAGA CTTTACTCGA CAACTGTTAA 220        230        240        250        260        270        280
AATCATCGGC TCGTATAATG TGTGGAATTG TGAGCGGATA ACAATTTCAC ACAGGAAACA GCGATGAGCT
TTAGTAGCCG AGCATATTAC ACACCTTAAC ACTCGCCTAT TGTTAAAGTG TGTCCTTTGT CGCTACTCGA 290        300        310        320        330        340        350
TGGCTGCAGG TCGAGTTCTA GATAACGAGG CGTAAAAAAT GAAAAGACA GCTATCGCAA TTGCAGTGGC
ACCGACGTCC AGCTCAAGAT CTATTGCTCC GCATTTTTTA CTTTTCTGT CGATAGCGTT AACGTCACCG 360        370        380        390        400        410        420
CTTGGCTCTG ACGTACGAGT CAGGAATTCA CTGGCCGTCG TTTTACAACG TCGTGACTGG GAAAACCCTG
GAACCGAGAC TGCATGCTCA GTCCTTAAGT GACCGGCAGC AAAATGTTGC AGCACTGACC CTTTTGGGAC 430        440        450        460        470        480        490
GCGTTACCCA ACTTAATCGC CTTGCAGCAC ATCCCCTTT CGCCAGCTGG CGTAATAGCG AAGAGGCCCG
CGCAATGGGT TGAATTAGCG GAACGTCGTG TAGGGGGAAA GCGGTCGACC GCATTATCGC TTCTCCGGGC 500        510        520        530        540        550        560
CACCGATCGC CCTTCCCAAC AGTTGCGCAG CCTGAATGGC GAATGGCGGTA TGATGCGGTA TTTTCTCCTT
GTGGCTAGCG GGAAGGGTTG TCAACGCGTC GGACTTACCG CTTACCGCGG ACTACGCCAT AAAAGAGGAA 570        580        590        600        610        620        630
ACGCATCTGT GCGGTATTTC ACACCGCATA AATTCCCTGT TTTGGCGGAT GAGAGAAGAT TTTCAGCCTG
TGCGTAGACA CGCCATAAAG TGTGGCGTAT TTAAGGGACA AAACCGCCTA CTCTCTTCTA AAAGTCGGAC 640        650        660        670        680        690        700
ATACAGATTA AATCAGAACG CAGAAGCGGT CTGATAAAAC AGAATTTGCC TGGCGGCAGT AGCGCGGTGG
TATGTCTAAT TTAGTCTTGC GTCTTCGCCA GACTATTTTG TCTTAAACGG ACCGCCGTCA TCGCGCCACC 710        720        730        740        750        760        770
TCCCACCTGA CCCCATGCCG AACTCAGAAG TGAAACGCCG TAGCGCCGAT GGTAGTGTGG GGTCTCCCCA
AGGGTGGACT GGGGTACGGC TTGAGTCTTC ACTTTGCGGC ATCGCGGCTA CCATCACACC CCAGAGGGGT 780        790        800        810        820        830        840
TGCGAGAGTA GGGAACTGCC AGGCATCAAA TAAAACGAAA GGCTCAGTCG AAAGACTGGG CCTTTCGTTT
ACGCTCTCAT CCCTTGACGG TCCGTAGTTT ATTTTGCTTT CCGAGTCAGC TTTCTGACCC GGAAAGCAAA 850        860        870        880        890        900        910
TATCTGTTGT TTGTCGGTGA ACGCTCTCCT GAGTAGGACA AATCCGCCGG GAGCGGATTT GAACGTTGCG
ATAGACAACA AACAGCCACT TGCGAGAGGA CTCATCCTGT TTAGGCGGCC CTCGCCTAAA CTTGCAACGC 920        930        940        950        960        970        980
AAGCAACGGC CCGGAGGGTG GCGGGCAGGA CGCCCGCCAT AAACTGCCAG GCATCAAATT AAGCAGAAGG
TTCGTTGCCG GGCCTCCCAC CGCCCGTCCT GCGGGCGGTA TTTGACGGTC CGTAGTTTAA TTCGTCTTCC 990       1000       1010       1020       1030       1040       1050
CCATCCTGAC GGATGGCCTT TTTGCGTTTC TACAAACTCT TCCTGTCGTC ATATCTACAA GCCATCCCCC
GGTAGGACTG CCTACCGGAA AAACGCAAAG ATGTTTGAGA AGGACAGCAG TATAGATGTT CGGTAGGGGG 1060       1070       1080       1090       1100       1110       1120
CACAGATACG GTAAACTAGC CTCGTTTTTG CATCAGGAAA GCAGGGAATT TATGGTGCAC TCTCAGTACA
GTGTCTATGC CATTTGATCG GAGCAAAAAC GTAGTCCTTT CGTCCCTTAA ATACCACGTG AGAGTCATGT 1130       1140       1150       1160       1170       1180       1190
ATCTGCTCTG ATGCCGCATA GTTAAGCCAG CCCCGACACC CGCCAACACC CGCTGACGCG CCCTGACGGG
TAGACGAGAC TACGGCGTAT CAATTCGGTC GGGGCTGTGG GCGGTTGTGG GCGACTGCGC GGGACTGCCC 1200       1210       1220       1230       1240       1250       1260
CTTGTCTGCT CCCGGCATCC GCTTACAGAC AAGCTGTGAC CGTCTCCGGG AGCTGCATGT GTCAGAGGTT
GAACAGACGA GGGCCGTAGG CGAATGTCTG TTCGACACTG GCAGAGGCCC TCGACGTACA CAGTCTCCAA 1270       1280       1290       1300       1310       1320       1330
TTCACCGTCA TCACCGAAAC GCGCGAGACG AAAGGGCCTC GTGATACGCC TATTTTTATA GGTTAATGTC
AAGTGGCAGT AGTGGCTTTG CGCGCTCTGC TTTCCCGGAG CACTATGCGG ATAAAAATAT CCAATTACAG 1340       1350       1360       1370       1380       1390       1400
```

Fig. 5(contd)

```
           1410       1420       1430       1440       1450       1460       1470
ATGATAATAA TGGTTTCTTA GACGTGAGGT TCTGTACCCG ACACCATCGA ATGGTGCAAA ACCTTTCGCG
TACTATTATT ACCAAAGAAT CTGCACTCCA AGACATGGGC TGTGGTAGCT TACCACGTTT TGGAAAGCGC 1410       1420       1430       1440       1450       1460       1470
GTATGGCATG ATAGCGCCCG GAAGAGAGTC AATTCAGGGT GGTGAATGTG AAACCAGTAA CGTTATACGA
CATACCGTAC TATCGCGGGC CTTCTCTCAG TTAAGTCCCA CCACTTACAC TTTGGTCATT GCAATATGCT 1480       1490       1500       1510       1520       1530       1540
TGTCGCAGAG TATGCCGGTG TCTCTTATCA GACCGTTTCC CGCGTGGTGA ACCAGGCCAG CCACGTTTCT
ACAGCGTCTC ATACGGCCAC AGAGAATAGT CTGGCAAAGG GCGCACCACT TGGTCCGGTC GGTGCAAAGA 1550       1560       1570       1580       1590       1600       1610
GCGAAAACGC GGGAAAAAGT GGAAGCGGCG ATGGCGGAGC TGAATTACAT TCCCAACCGC GTGGCACAAC
CGCTTTTGCG CCCTTTTTCA CCTTCGCCGC TACCGCCTCG ACTTAATGTA AGGGTTGGCG CACCGTGTTG 1620       1630       1640       1650       1660       1670       1680
AACTGGCGGG CAAACAGTCG TTGCTGATTG GCGTTGCCAC CTCCAGTCTG GCCCTGCACG CGCCGTCGCA
TTGACCGCCC GTTTGTCAGC AACGACTAAC CGCAACGGTG GAGGTCAGAC CGGGACGTGC GCGGCAGCGT 1690       1700       1710       1720       1730       1740       1750
AATTGTCGCG GCGATTAAAT CTCGCGCCGA TCAACTGGGT GCCAGCGTGG TGGTGTCGAT GGTAGAACGA
TTAACAGCGC CGCTAATTTA GAGCGCGGCT AGTTGACCCA CGGTCGCACC ACCACAGCTA CCATCTTGCT 1760       1770       1780       1790       1800       1810       1820
AGCGGCGTCG AAGCCTGTAA AGCGGCGGTG CACAATCTTC TCGCGCAACG CGTCAGTGGG CTGATCATTA
TCGCCGCAGC TTCGGACATT TCGCCGCCAC GTGTTAGAAG AGCGCGTTGC GCAGTCACCC GACTAGTAAT 1830       1840       1850       1860       1870       1880       1890
ACTATCCGCT GGATGACCAG GATGCCATTG CTGTGGAAGC TGCCTGCACT AATGTTCCGG CGTTATTTCT
TGATAGGCGA CCTACTGGTC CTACGGTAAC GACACCTTCG ACGGACGTGA TTACAAGGCC GCAATAAAGA 1900       1910       1920       1930       1940       1950       1960
TGATGTCTCT GACCAGACAC CCATCAACAG TATTATTTTC TCCCATGAAG ACGGTACGCG ACTGGGCGTG
ACTACAGAGA CTGGTCTGTG GGTAGTTGTC ATAATAAAAG AGGGTACTTC TGCCATGCGC TGACCCGCAC 1970       1980       1990       2000       2010       2020       2030
GAGCATCTGG TCGCATTGGG TCACCAGCAA ATCGCGCTGT TAGCGGGCCC ATTAAGTTCT GTCTCGGCGC
CTCGTAGACC AGCGTAACCC AGTGGTCGTT TAGCGCGACA ATCGCCCGGG TAATTCAAGA CAGAGCCGCG 2040       2050       2060       2070       2080       2090       2100
GTCTGCGTCT GGCTGGCTGG CATAAATATC TCACTGCACA TCAAATTCAG CCGATAGCGG AACGGGAAGG
CAGACGCAGA CCGACCGACC GTATTTATAG AGTGAGCGTT AGTTTAAGTC GGCTATCGCC TTGCCCTTCC 2110       2120       2130       2140       2150       2160       2170
CGACTGGAGT GCCATGTCCG GTTTTCAACA AACCATGCAA ATGCTGAATG AGGGCATCGT TCCCACTGCG
GCTGACCTCA CGGTACAGGC CAAAAGTTGT TTGGTACGTT TACGACTTAC TCCCGTAGCA AGGGTGACGC 2180       2190       2200       2210       2220       2230       2240
ATGCTGGTTG CCAACGATCA GATGGCGCTG GGCGCAATGC GCGCCATTAC CGAGTCCGGG CTGCGCGTTG
TACGACCAAC GGTTGCTAGT CTACCGCGAC CCGCGTTACG CGCGGTAATG GCTCAGGCCC GACGCGCAAC 2250       2260       2270       2280       2290       2300       2310
GTGCGGATAT CTCGGTAGTG GGATACGACG ATACCGAAGA CAGCTCATGT TATATCCCGC CGTTAACCAC
CACGCCTATA GAGCCATCAC CCTATGCTGC TATGGCTTCT GTCGAGTACA ATATAGGGCG GCAATTGGTG 2320       2330       2340       2350       2360       2370       2380
CATCAAACAG GATTTTCGCC TGCTGGGGCA AACCAGCGTG GACCGCTTGC TGCAACTCTC TCAGGGCCAG
GTAGTTTGTC CTAAAAGCGG ACGACCCCGT TTGGTCGCAC CTGGCGAACG ACGTTGAGAG AGTCCCGGTC 2390       2400       2410       2420       2430       2440       2450
GCGGTGAAGG GCAATCAGCT GTTGCCCGTC TCACTGGTGA AAAGAAAAAC CACCCTGGCG CCCAATACGC
CGCCACTTCC CGTTAGTCGA CAACGGGCAG AGTGACCACT TTTCTTTTTG GTGGGACCGC GGGTTATGCG 2460       2470       2480       2490       2500       2510       2520
AAACCGCCTC TCCCCGCGCG TTGGCCGATT CATTAATGCA GCTGGCACGA CAGGTTTCCC GACTGGAAAG
TTTGGCGGAG AGGGGCGCGC AACCGGCTAA GTAATTACGT CGACCGTGCT GTCCAAAGGG CTGACCTTTC 2530       2540       2550       2560       2570       2580       2590
CGGGCAGTGA GCGCAACGCA ATTAATGTAA GTTAGCTCAC TCATTAGGCA CCCCAGGCTT TACACTTTAT
GCCCGTCACT CGCGTTGCGT TAATTACATT CAATCGAGTG AGTAATCCGT GGGGTCCGAA ATGTGAAATA 2600       2610       2620       2630       2640       2650       2660
GCTTCCGACC TGCAAGAACC TCACGTCAGG TGGCACTTTT CGGGGAAATG TGCGCGGAAC CCCTATTTGT
CGAAGGCTGG ACGTTCTTGG AGTGCAGTCC ACCGTGAAAA GCCCCTTTAC ACGCGCCTTG GGGATAAACA 2670       2680       2690       2700       2710       2720       2730
TTATTTTTCT AAATACATTC AAATATGTAT CCGCTCATGA GACAATAACC CTGATAAATG CTTCAATAAT
AATAAAAGA  TTTATGTAAG TTTATACATA GGCGAGTACT CTGTTATTGG GACTATTTAC GAAGTTATTA 2740       2750       2760       2770       2780       2790       2800
CTGTCCCTCC TGTTCAGCTA CTGACGGGGT GGTGCGTAAC GGCAAAAGCA CCGCCGGACA TCAGCGCTAG
```

Fig. 5(contd)

```
          GACAGGGAGG ACAAGTCGAT GACTGCCCCA CCACGCATTG CCGTTTTCGT GGCGGCCTGT AGTCGCGATC 2810       2820       2830       2840       2850       2860       2870
CGGAGTGTAT ACTGGCTTAC TATGTTGGCA CTGATGAGGG TGTCAGTGAA GTGCTTCATG TGGCAGGAGA
GCCTCACATA TGACCGAATG ATACAACCGT GACTACTCCC ACAGTCACTT CACGAAGTAC ACCGTCCTCT 2880       2890       2900       2910       2920       2930       2940
AAAAAGGCTG CACCGGTGCG TCAGCAGAAT ATGTGATACA GGATATATTC CGCTTCCTCG CTCACTGACT
TTTTTCCGAC GTGGCCACGC AGTCGTCTTA TACACTATGT CCTATATAAG GCGAAGGAGC GAGTGACTGA 2950       2960       2970       2980       2990       3000       3010
CGCTACGCTC GGTCGTTCGA CTGCGGCGAG CGGAAATGGC TTACGAACGG GGCGGAGATT TCCTGGAAGA
GCGATGCGAG CCAGCAAGCT GACGCCGCTC GCCTTTACCG AATGCTTGCC CCGCCTCTAA AGGACCTTCT 3020       3030       3040       3050       3060       3070       3080
TGCCAGGAAG ATACTTAACA GGGAAGTGAG AGGGCCGCGG CAAAGCCGTT TTTCCATAGG CTCCGCCCCC
ACGGTCCTTC TATGAATTGT CCCTTCACTC TCCCGGCGCC GTTTCGGCAA AAAGGTATCC GAGGCGGGGG 3090       3100       3110       3120       3130       3140       3150
CTGACAAGCA TCACGAAATC TGACGCTCAA ATCAGTGGTG GCGAAACCCG ACAGGACTAT AAAGATACCA
GACTGTTCGT AGTGCTTTAG ACTGCGAGTT TAGTCACCAC CGCTTTGGGC TGTCCTGATA TTTCTATGGT 3160       3170       3180       3190       3200       3210       3220
GGCGTTTCCC CCTGGCGGCT CCCTCGTGCG CTCTCCTGTT CCTGCCTTTC GGTTTACCGG TGTCATTCCG
CCGCAAAGGG GGACCGCCGA GGGAGCACGC GAGAGGACAA GGACGGAAAG CCAAATGGCC ACAGTAAGGC 3230       3240       3250       3260       3270       3280       3290
CTGTTATGGC CGCGTTTGTC TCATTCCACG CCTGACACTC AGTTCCGGGT AGGCAGTTCG CTCCAAGCTG
GACAATACCG GCGCAAACAG AGTAAGGTGC GGACTGTGAG TCAAGGCCCA TCCGTCAAGC GAGGTTCGAC 3300       3310       3320       3330       3340       3350       3360
GACTGTATGC ACGAACCGCC CGTTCAGTCC GACCGCTGCA CCTTATCCGG TAACTATCGT CTTGAGTCCA
CTGACATACG TGCTTGGGGG GCAAGTCAGG CTGGCGACGC GGAATAGGCC ATTGATAGCA GAACTCAGGT 3370       3380       3390       3400       3410       3420       3430
ACCCGGAAAG ACATGCAAAA GCACCACTGG CAGCAGCCAC TGGTAATTGA TTTAGAGGAG TTAGTCTTGA
TGGGCCTTTC TGTACGTTTT CGTGGTGACC GTCGTCGGTG ACCATTAACT AAATCTCCTC AATCAGAACT 3440       3450       3460       3470       3480       3490       3500
AGTCATGCGC CGGTTAAGGC TAAACTGAAA GGACAAGTTT TGGTGACTGC GCTCCTCCAA GCCAGTTACC
TCAGTACGCG GCCAATTCCG ATTTGACTTT CCTGTTCAAA ACCACTGACG CGAGGAGGTT CGGTCAATGG 3510       3520       3530       3540       3550       3560       3570
TCGGTTCAAA GAGTTGGTAG CTCAGAGAAC CTTCGAAAAA CCGCCCTGCA AGGCGGTTTT TTCGTTTTCA
AGCCAAGTTT CTCAACCATC GAGTCTCTTG GAAGCTTTTT GGCGGGACGT TCCGCCAAAA AAGCAAAAGT 3580       3590       3600       3610       3620       3630       3640
GAGCAAGAGA TTACGCGCAG ACCAAAACGA TCTCAAGAAG ATCATCTTAT TAATCAGATA AAATATTTCT
CTCGTTCTCT AATGCGCGTC TGGTTTTGCT AGAGTTCTTC TAGTAGAATA ATTAGTCTAT TTTATAAAGA 3650       3660       3670       3680       3690       3700       3710
AGATTTCAGT GCAATTTATC TCTTCAAATG TAGCACCTGA AGTCAGCCCC ATACGATATA AGTTGTAATT
TCTAAAGTCA CGTTAAATAG AGAAGTTTAC ATCGTGGACT TCAGTCGGGG TATGCTATAT TCAACATTAA 3720       3730       3740       3750       3760       3770       3780
CTCATGTTTG ACAGCTTATC ATCGATAAGC TTTAATGCGG TAGTTTATCA CAGTTAAATT GCTAACGCAG
GAGTACAAAC TGTCGAATAG TAGCTATTCG AAATTACGCC ATCAAATAGT GTCAATTTAA CGATTGCGTC 3790       3800       3810       3820       3830       3840       3850
TCAGGCACCG TGTATGAAAT CTAACAATGC GCTCATCGTC ATCCTCGGCA CCGTCACCCT GGATGCTGTA
AGTCCGTGGC ACATACTTTA GATTGTTACG CGAGTAGCAG TAGGAGCCGT GGCAGTGGGA CCTACGACAT 3860       3870       3880       3890       3900       3910       3920
GGCATAGGCT TGGTTATGCC GGTACTGCCG GGCCTCTTGC GGGATATCGT CCATTCCGAC AGCATCGCCA
CCGTATCCGA ACCAATACGG CCATGACGGC CCGGAGAACG CCCTATAGCA GGTAAGGCTG TCGTAGCGGT 3930       3940       3950       3960       3970       3980       3990
GTCACTATGG CGTGCTGCTA GCGCTATATG CGTTGATGCA ATTTCTATGC GCACCCGTTC TCGGAGCACT
CAGTGATACC GCACGACGAT CGCGATATAC GCAACTACGT TAAAGATACG CGTGGGCAAG AGCCTCGTGA 4000       4010       4020       4030       4040       4050       4060
GTCCGACCGC TTTGCCGCC GCCCAGTCCT GCTCGCTTCG CTACTTGGAG CCACTATCGA CTACGCGATC
CAGGCTGGCG AAACCGGCGG CGGGTCAGGA CGAGCGAAGC GATGAACCTC GGTGATAGCT GATGCGCTAG 4070       4080       4090       4100       4110       4120       4130
ATGGCGACCA CACCCGTCCT GTGGATCCTC TACGCCGGAC GCATCGTGGC CGGCATCACC GGCGCCACAG
TACCGCTGGT GTGGGCAGGA CACCTAGGAG ATGCGGCCTG CGTAGCACCG GCCGTAGTGG CCGCGGTGTC 4140       4150       4160       4170       4180       4190       4200
GTGCGGTTGC TGGCGCCTAT ATCGCCGACA TCACCGATGG GGAAGATCGG GCTCGCCACT TCGGGCTCAT
CACGCCAACG ACCGCGGATA TAGCGGCTGT AGTGGCTACC CCTTCTAGCC CGAGCGGTGA AGCCCGAGTA
```

```
           4210       4220       4230       4240       4250       4260       4270
      GAGCGCTTGT TTCGGCGTGG GTATGGTGGC AGGCCCCGTG GCCGGGGGAC TGTTGGGCGC CATCTCCTTG
      CTCGCGAACA AAGCCGCACC CATACCACCG TCCGGGCAC CGGCCCCCTG ACAACCCGCG GTAGAGGAAC 4280       4290       4300       4310       4320       4330       4340
      CATGCACCAT TCCTTGCGGC GGCGGTGCTC AACGGCCTCA ACCTACTACT GGGCTGCTTC CTAATGCAGG
      GTACGTGGTA AGGAACGCCG CCGCCACGAG TTGCCGGAGT TGGATGATGA CCCGACGAAG GATTACGTCC 4350       4360       4370       4380       4390       4400       4410
      AGTCGCATAA GGGAGAGCGT CGACCGATGC CCTTGAGAGC CTTCAACCCA GTCAGCTCCT TCCGGTGGGC
      TCAGCGTATT CCCTCTCGCA GCTGGCTACG GGAACTCTCG GAAGTTGGGT CAGTCGAGGA AGGCCACCCG 4420       4430       4440       4450       4460       4470       4480
      GCGGGGCATG ACTATCGTCG CCGCACTTAT GACTGTCTTC TTTATCATGC AACTCGTAGG ACAGGTGCCG
      CGCCCCGTAC TGATAGCAGC GGCGTGAATA CTGACAGAAG AAATAGTACG TTGAGCATCC TGTCCACGGC 4490       4500       4510       4520       4530       4540       4550
      GCAGCGCTCT GGGTCATTTT CGGCGAGGAC CGCTTTCGCT GGAGCGCGAC GATGATCGGC CTGTCGCTTG
      CGTCGCGAGA CCCAGTAAAA GCCGCTCCTG GCGAAAGCGA CCTCGCGCTG CTACTAGCCG GACAGCGAAC 4560       4570       4580       4590       4600       4610       4620
      CGGTATTCGG AATCTTGCAC GCCCTCGCTC AAGCCTTCGT CACTGGTCCC GCCACCAAAC GTTTCGGCGA
      GCCATAAGCC TTAGAACGTG CGGGAGCGAG TTCGAAGCA GTGACCAGGG CGGTGGTTTG CAAAGCCGCT 4630       4640       4650       4660       4670       4680       4690
      GAAGCAGGCC ATTATCGCCG GCATGGCGGC CGACGCGCTG GGCTACGTCT TGCTGGCGTT CGCGACGCGA
      CTTCGTCCGG TAATAGCGGC CGTACCGCCG GCTGCGCGAC CCGATGCAGA ACGACCGCAA GCGCTGCGCT 4700       4710       4720       4730       4740       4750       4760
      GGCTGGATGG CCTTCCCCAT TATGATTCTT CTCGCTTCCG GCGGCATCGG GATGCCCGCG TTGCAGGCCA
      CCGACCTACC GGAAGGGGTA ATACTAAGAA GAGCGAAGGC CGCCGTAGCC CTACGGGCGC AACGTCCGGT 4770       4780       4790       4800       4810       4820       4830
      TGCTGTCCAG GCAGGTAGAT GACGACCATC AGGGACAGCT TCAAGGATCG CTCGCGGCTC TTACCAGCCT
      ACGACAGGTC CGTCCATCTA CTGCTGGTAG TCCCTGTCGA AGTTCCTAGC GAGCGCCGAG AATGGTCGGA 4840       4850       4860       4870       4880       4890       4900
      AACTTCGATC ATTGGACCGC TGATCGTCAC GGCGATTTAT GCCGCCTCGG CGAGCACATG GAACGGGTTG
      TTGAAGCTAG TAACCTGGCG ACTAGCAGTG CCGCTAAATA CGGCGGAGCC GCTCGTGTAC CTTGCCCAAC 4910       4920       4930       4940       4950       4960       4970
      GCATGGATTG TAGGCGCCGC CCTATACCTT GTCTGCCTCC CCGCGTTGCG TCGCGGTGCA TGGAGCCGGG
      CGTACCTAAC ATCCGCGGCG GGATATGGAA CAGACGGAGG GGCGCAACGC AGCGCCACGT ACCTCGGCCC 4980       4990       5000       5010       5020       5030       5040
      CCACCTCGAC CTGAATGGAA GCCGGCGGCA CCTCGCTAAC GGATTCACCA CTCCAAGAAT TGGAGCCAAT
      GGTGGAGCTG GACTTACCTT CGGCCGCCGT GGAGCGATTG CCTAAGTGGT GAGGTTCTTA ACCTCGGTTA 5050       5060       5070
      CAATTCTTGC GGAGAACTGT GAATGCGCAA ACCAACC
      GTTAAGAACG CCTCTTGACA CTTACGCGTT TGGTTGG
```

*Fig. 5(contd)*

Fig. 9

OLIGONUCLEOTIDE CASSETTES ENCODING DIFFERENT INTERGENIC SEQUENCES FOR E. Coli Fab' EXPRESSION

IGS CASSETTE-1:  Intergenic space = -1
SacI                                                                                          MunI
G, AGC, TCA, CCA, GTA, ACA, AAA, AGT, TTT, AAT, AGA, GGA, GAG, TGT, TAATG, AAG, AAG, ACT, GCT, ATA, GCA, ATT, G S    S    P    V    T    K    S    F    N    R    G    E    C    * M    K    K    T    A    I    A    I
End of c-Kappa sequence ->                                         Start of OmpA sequence ->

IGS CASSETTE-2:  Intergenic space = +1

G, AGC, TCA, CCA, GTA, ACA, AAA, AGT, TTT, AAT, AGA, GGG, GAG, TGT, TAA AATG, AAG, AAG, ACT, GCT, ATA, GCA, ATT, G

S    S    P    V    T    K    S    F    N    R    G    E    C    *    M    K    K    T    A    I    A    I

IGS CASSETTE-3:  Intergenic space = +13

G, AGC, TCA, CCA, GTA, ACA, AAA, AGT, TTT, AAT, AGA, GGA, GAG, TGT, TGA GGAGGAAAAAAAATG, AAG, AAA, ACT, GCT, ATA, GCA, ATT, G

S    S    P    V    T    K    S    F    N    R    G    E    C    *              M    K    K    T    A    I    A    I

IGS CASSETTE-4:  Intergenic space = +13

G, AGC, TCA, CCA, GTA, ACA, AAA, AGT, TTT, AAT, AGA, GGA, GAG, TGT, TGA CGAGGATTATATAATG, AAG, AAA, ACT, GCT, ATA, GCA, ATT, G

S    S    P    V    T    K    S    F    N    R    G    E    C    *              M    K    K    T    A    I    A    I

Periplasmic Fab' accumulation - IGS variants g163 Fab' expression (shake flask)

Comparison of pTTO(gA33 IGS-2) and pTTO(gA33 IGS-3) Fab' expression in 1L fermentation

EXPRESSION CONTROL USING VARIABLE INTERGENIC SEQUENCES

CROSS-REFERENCE TO RELATED APPLICATIONS

The present application is a 35 U.S.C. 371 National Stage Application of International Application No. PCT/GB02/05466, International Filing Date: Dec. 5, 2002, which claims priority under 35 U.S.C. 119(a) to Great Britain Application No. 0129105.3, Filing Date: Dec. 5, 2001, which is incorporated herein by reference in its entirety.

FIELD OF THE INVENTION

The present invention relates to a method of production of antibodies wherein the heavy and light chains of a particular antibody molecule are encoded by the DNA present in a dicistronic message in which the two cistrons are linked by an optimised intergenic sequence.

BACKGROUND TO THE INVENTION

The ability of antibodies to recognise specific antigens has made them highly useful and effective tools in medicine and biotechnology. Antibodies specific for antigens on selected types of cell have been used to target these antibodies to the selected cell. The binding of antibodies to receptors on cells has been found in some cases to affect the function of the cell. Therapeutic and diagnostic agents have also been conjugated to antibodies to specifically target these agents to selected cells. This technique has been used particularly in the targeting of cancer cells. Antibodies have also been used to target antigens on virally- or bacterially-infected cells, to target other molecules, such as TNFα, or for use in assays. In biotechnology, antibodies have many uses such as probes, in purification and in catalysis.

All whole antibody molecules consist of four polypeptide chains—two identical heavy chains and two identical light chains. Each chain comprises both variable and constant domains. Light chains comprise two domains: $V_L$ and $C_L$, whilst heavy chains comprise at least five domains: $V_H$, $C_H1$, hinge, $C_H2$ and $C_H3$ and an optional $C_H4$. The four chains are always organised in the same general fashion: the two heavy chains are linked together by at least one disulphide bond and each heavy chain is also linked to one of the light chains by a disulphide bond such that both light chains are linked to a separate heavy chain.

Whole antibody molecules are roughly Y-shaped and consist essentially of two main functional parts. The first functional part is responsible for the recognition of specific antigens and is formed by the upper part of the arms of the Y. The antigen binding region in each part comprises one $V_H$ domain and one $V_L$ domain. Each variable domain contains three hypervariable regions which, together with the three hypervariable regions in the other chain, form the antigen-binding site. These hypervariable regions are known as complementarity determining regions (CDR1, CDR2 and CDR3). The CDRs, which form loops, are supported on framework regions. Due to its variability between antibodies, the regions comprising $V_H$ and $V_L$ are known as the 'V' regions.

The second functional part is responsible for triggering the effector functions of other cells that will dispose of the antigen recognised by the antibody and is formed by the lower parts of the arms and the stem of the Y. This region is known as the constant 'C' region due to its relative constancy. It comprises the $C_L$ domains and all the heavy chain C domains.

There are two types of light chain: κ and λ, and five types of heavy chain: α, δ, γ, ε and μ. The class of the antibody is determined by the type of heavy chain it has: IgA, IgD, IgE, IgG and IgM respectively.

Antibody fragments, which have had part of their constant region removed by enzymatic cleavage, are also used in medicine and biotechnology. These include Fab, Fab', F(ab')$_2$ and Fv fragments.

It is known to direct production of large amounts of monoclonal antibodies (having a particular antigen-specificity) by fusing an antibody-producing spleen cell with a myeloma cell, resulting in a hybridoma (Kohler, G. and Milstein, C. Continuous cultures of fused cells secreting antibody of predefined specificity. Nature, 256, 495-497 (1975)). However, such antibodies are unsuitable for use in human therapy as they are immunogenic in humans. Most monoclonal antibodies are produced by non-human cells.

Recombinant DNA techniques have been developed which enable the useful properties of more than one antibody to be combined to make one new antibody. The production of chimeric antibodies, in which the antigen-binding site comprising the complete V region of one antibody is linked to the constant region from a different antibody, is described in EP-A-0120694 (Celltech Limited), EP-A-0125023 (Genentech Inc. and City of Hope), EP-A-0171496 (Research Development Corporation, Japan), EP-A-0173494 (Stanford University) and WO-A-86/01533 (Celltech Limited).

WO-A-86/01533, for example, describes the preparation of a chimeric antibody in which murine V regions are joined to human constant regions. However, the large proportion of residues in chimeric non-human/human antibodies which are derived from the non-human donor result in the possibility of the antibody eliciting a potentially harmful immunological response, particularly if administered over a prolonged period (Begent et al., Br. J. Cancer, 62, 487 (1990)).

Antibody 'humanisation' is a technique which makes non-human/human chimeric antibodies appear more like human antibodies to the human immune system and has been developed in an attempt to overcome the unwanted immunological response mentioned above. EP-A-0239400 (Winter) describes how, instead of using a complete murine variable region, the CDRs of a murine monoclonal antibody are grafted onto the framework regions of the variable domains of a human antibody. Thus, it is only the CDRs forming the antigen-binding domain itself that are murine and the other residues are human.

Reichmann et al., ("Reshaping human anitbodies for therapy", Nature, 332, 323-324, 1988) found it to be advantageous to convert other human residues in the variable domain to their non-human donor counterparts to improve antigen-binding activity. Such a residue was found at position 27 of the human heavy chain, which, when converted from the human serine to the corresponding rat residue (phenylalanine), resulted in improved antigen-binding ability. Another such residue was found at position 30. However, a construct which contained a human serine to rat tyrosine change at position 30 of the heavy chain in addition to the change at position 27 mentioned above, did not have a significantly altered binding activity over the humanised antibody with the serine to phenylalanine change at position 27 alone.

Heavy chain residues 27 and 30 are within the structural loop adjacent to CDR1. Queen et al., (WO 90/07861) conjectured that other residues which interact with the CDRs are also important in determining antigen-binding affinity. With this in mind, Queen et al., proposed four criteria for determining which residues should come from the donor and which from the acceptor when designing humanised antibodies. In a more definitive analysis, Adair et al., (WO 91/09967) disclosed a hierarchy of residue numbers that will enable a humanised antibody to be designed.

A number of reviews discussing CDR-grafted antibodies have been published including Vaughan et al., (Nature Biotechnology, 16, 535-539, 1998).

Antibody conjugates, in which the constant region has been fused to effector or reporter molecules which may act as therapeutic or diagnostic agents, have also been described (WO 95/01155, U.S. Pat. Nos. 3,927,193, 4,331,647, 4,348,376, 4,361,544, 468,457, 4,444,744, 4,460,459 and U.S. Pat. No. 4,460,561 and reviews by Waldmann, T. A., Science, 252, 1657, (1991); Koppel, G. A., Bioconjug. Chem., 1, 13, (1990); Oeltmann, T. N. and Frankel, A. E., FASEB J., 5, 2334, (1991); and van den Bergh, H. E., Chemistry in Britain, May 1986, 430-439).

It was known to produce normal, chimeric or humanised antibodies by transfecting a suitable host cell with two expression vectors, one containing a DNA sequence encoding the heavy chain and one containing a DNA sequence encoding the light chain of the required antibody (WO-A-91/09967). Alternatively, it was known to transfect a suitable host cell with an expression vector that contains both the DNA sequence encoding the heavy chain and the DNA sequence encoding the light chain of the required antibody. In the latter example, the DNA sequences encoding the heavy chain and the light chain are either under the control of their own individual promoters (WO-A-91/09967) or are present in a dicistronic message (Better, M., Paul Chang, C., Robinson, R. R. and Horwitz, A. H. *Escherichia coli*: Secretion of an Active Chimeric Antibody Fragment. Science, 240, 1041-1043 (1988)).

A dicistronic message was used by Better et al., to produce a chimeric mouse L6 Fab antibody directed towards a ganglioside antigen expressed on the surface of many human carcinomas. A dicistronic message was chosen in this case in an attempt to ensure that both the truncated heavy chains (Fd) and the κ light chains were translated in close physical proximity so that they would assemble correctly and be secreted. Dicistronic messages are only able to function in bacteria whereas the 'one gene, one promoter' concept functions in both mammals and bacteria. In a dicistronic message, a promoter is associated only with the first cistron. The second cistron is transcribed by the polymerase 'reading through' to the second cistron such that both cistrons are represented by a single RNA molecule. The two coding DNA cistrons are separated by a stretch of DNA known as an 'intergenic sequence' or 'IGS'. This IGS region is also present in the RNA molecule that is transcribed from the DNA.

Optimisation of the translational initiation rate has for some time been recognised as essential for high level expression of secreted heterologous proteins in *E. coli* (Simmons, L. and Yansura, D. Nature Biotech, 14, 629-634 (1996)). However, different Fab's have different framework and CDR sequences which confer different properties to the molecule, including differences in the ease (or rate) of folding within the *E. coli* periplasm (Knappik, A. and Pluckthun, A. Prot Eng 8, 81-89 (1995)). For example, a Fab' which folds into its native conformation easily and rapidly within the *E. coli* periplasm is likely to be 'tolerated' at a high level and rapid translation can be accommodated to achieve high-level accumulation. A Fab' which folds more poorly is likely to be tolerated less well by the host bacterium if rapidly translated, potentially saturating host folding/secretion machinery and having a deleterious effect on host cell physiology.

Thus, when producing antibodies using a host cell-expression vector system, a high level of expression of a particular antibody may be tolerated, but for a different antibody, a high level of expression might prove toxic to the cell, perhaps because of different efficiencies of secretion or folding.

The level of expression of a particular antibody is determined by the amount of heavy and light chains present. For maximal production, the ratio of heavy chains to light chains should be balanced, such as equal quantities of both. However, if either the heavy or the light chain is present in a lesser amount, this will limit the amount of antibody produced. Accumulation of excess heavy chain is likely to be particularly poorly tolerated.

In the case of an antibody encoded by a dicistronic message, the upstream cistron may contain either the DNA coding for the heavy chain or the light chain of an antibody with a particular antigen specificity. The downstream cistron would then encode the respective light chain or heavy chain partner. It would be advantageous if the level of expression of the antibody chain corresponding to the coding DNA in the downstream cistron of a dicistronic message could be regulated to produce the desired level of expression for a particular antibody.

SUMMARY OF THE INVENTION

In a first aspect, the present invention provides a dicistronic message for producing an antibody molecule with a particular antigen-binding specificity, in which the upstream cistron contains DNA coding for either the heavy chain or the light chain of the antibody and the downstream cistron contains DNA coding for the corresponding light chain or heavy chain respectively, characterised in that the two cistrons are linked by an optimised intergenic sequence (IGS) and wherein the antibody produced is not an anti-TNFα antibody (for example, see PCT/GB01/02477) or an anti-human kinase insert domain-containing receptor (anti-KDR) antibody (for example, see PCT/GB02/004619).

Preferably, the upstream cistron codes for the light chain of the antibody and the downstream cistron codes for the corresponding heavy chain.

The IGS has been optimised to regulate the expression level of the antibody chain corresponding to the downstream cistron in the dicistronic message in order to achieve the desired expression level for the particular antibody.

In this specification, the length of the IGS is defined as the number of nucleotides between the stop codon of the upstream cistron and start codon of the downstream cistron (non-inclusive). The length of the IGS is involved in determining the rate of translation of the part of the RNA which corresponds to the downstream cistron. For example, a short intergenic sequence may result in very tight translational coupling between the heavy and the light chains, in that the translating ribosome may not fully dissociate from the mRNA after completing synthesis of the antibody chain encoded by the upstream cistron before initiating synthesis of the antibody chain encoded by the downstream cistron (Adhin, M. and van Duin, J. J. Mol. Biol., 213, 811-818 (1990); Andre, A. et al., FEBS Letts., 468, 73-78 (2000)). Such a process, termed translational re-initiation, will only occur if the stop codon of the upstream gene is very close to the start codon of the downstream gene. Due to kinetic considerations, this will result in increased expression of the polypeptide encoded by the downstream cistron since translation will not require a ribosome to bind to the mRNA molecule in its IGS.

If there is too much separation between the two genes, the ribosome will dissociate after completion of synthesis of the upstream cistron, requiring a new ribosome to initiate translation of the downstream cistron. In general, this will reduce the efficiency of translational initiation.

The presence of a Shine Dalgarno (SD) ribosome binding site (complementary to 16S rRNA) in the IGS allows a ribosome to bind to this IGS sequence and translate the downstream cistron. Where the distance between cistrons is sufficiently short to permit translational reinitiation to occur, there is some evidence to suggest that the presence of a SD site within the upstream cistron can increase the efficiency of translational initiation of the downstream cistron (Spanjaard, R. A. and van Duin, J. Nucl. Acids Res., 17, 5501-5507 (1989)).

There are several features of the SD site and the nucleotide sequence between the end of the SD site and the AUG initiation codon which have an influence on the strength of translational initiation (reviewed in Makrides, S. Microbiol. Revs., 60, 512-538 (1996)). The distance between the SD site and the AUG start codon of the downstream cistron is one such feature, as is the 'strength' of the SD site itself. An SD site that is 100% complementary to the 16S rRNA sequence that binds to it will in general result in greater expression than if the SD site is only partly complementary to the 16S rRNA sequence.

The sequence of the region between the SD sequence and the start codon is another important determinant of the rate of translation of the downstream cistron. The distance and sequence affect the potential secondary structure of mRNA around the start codon (reviewed in Makrides, S. Microbiol. Revs., 60, 512-538 (1996)). The start codon should be in a 'loop' and not constrained within a 'stem', while the reverse applies to the SD sequence. Thus by modifying the sequence and length of the IGS it is possible to modify the extent of translational coupling and/or the strength of translational initiation and therefore the level of translation of the downstream cistron and the subsequent rate of accumulation of the antibody chain it encodes.

The IGS of the dicistronic message of the present invention has been modified with respect to length, sequence and secondary structure such that optimal translational coupling of the two cistrons is achieved.

The optimal IGS sequence for use in the present invention can be empirically determined using the following method. The method comprises constructing a series of suitable expression vectors containing a series of IGS variants into which antibody molecules can be inserted for testing. Empirical testing of each IGS sequence for each antibody can be achieved by transforming the expression vector into a suitable host and analysing antibody expression and yield. The suite of IGS sequences described in the present application, which vary in length and sequence, can be used to construct such vectors from which the optimal IGS sequence for a particular antibody molecule can be selected. Said sequences include IGS sequences 1-4.

In a preferred embodiment, the IGS has been optimised such that maximum expression of the antibody chain encoded by the downstream cistron is achieved. This results in a maximal level of expression of the particular antibody as the amount of the antibody chain encoded by the downstream cistron is not limiting.

In a further embodiment, the IGS has been optimised such that the rate of translational initiation for translation of the downstream cistron is as high as possible.

In a further embodiment, the IGS has been optimised such that the rate of translational initiation for translation of the downstream cistron is not at the greatest possible achievable rate.

In a further embodiment, the IGS has been optimised such that the rate of translational initiation for translation of the downstream cistron is at a low rate.

The dicistronic message of the present invention codes for the heavy chain and the light chain of a particular antibody molecule. The antibody may be a whole antibody or in particular a fragment thereof, such as a Fab or a Fab' fragment. The antibody may also be a chimeric or a humanised antibody.

The dicistronic message of the present invention may comprise synthetic DNA, cDNA or genomic DNA, or any combination thereof.

The coding DNA sequence for a particular antibody can be obtained by methods well known to those skilled in the art. For example, DNA sequences coding for part or all of the antibody heavy and light chains may be synthesised as desired from the determined DNA sequences or on the basis of the corresponding amino acid sequences.

Standard techniques of molecular biology may be used to prepare DNA sequences coding for the heavy and light chains of specific antibody molecules to be linked by the IGS in a dicistronic message of the present invention. Desired DNA sequences may be synthesised completely or in part using oligonucleotide synthesis techniques. Site-directed mutagenesis and polymerase chain reaction (PCR) techniques may be used as appropriate.

The dicistronic message of the present invention may contain a DNA sequence encoding an effector or reporter protein that is fused to the DNA sequence encoding one of the antibody chains.

The dicistronic message of the present invention may also contain a DNA sequence encoding a peptide linkage which is fused to the DNA sequence encoding one of the antibody chains such that it will allow the subsequent attachment of an effector or reporter protein or molecule to the antibody expressed from the discistronic message.

The dicistronic message of the present invention may also contain a secretory signal sequence that is fused upstream of the DNA sequence encoding one or both of the antibody chains in order to allow targeting of the antibody chains to the periplasm or to outside the cell.

Preferably, the secretory signal sequence is an OmpA peptide sequence.

In a second aspect, the invention provides an expression vector containing a dicistronic message according to the first aspect of the present invention.

Preferably, the expression vector backbone is pTTO. The pTTO expression vector is designed to give rise to soluble, periplasmic accumulation of recombinant proteins in E. coli. This vector has the following main features:

(i) Tetracycline resistance marker—antibiotic not inactivated by the product of resistance gene, hence selection for plasmid-containing cells is maintained;

(ii) Low copy number—origin of replication derived from plasmid p15A, which is compatible with plasmids containing colE1 derived replicons;

(iii) Strong, inducible tac promoter for transcription of cloned gene(s); (iv) LacIq gene—gives constitutive expression of the lac repressor protein, maintaining the tac promoter in the repressed state until induction with IPTG/allolactose;

(v) OmpA signal sequence—gives periplasmic secretion of cloned gene(s); and (vi) Translational coupling of OmpA signal sequence to a short lacZ peptide, giving efficient initiation of translation.

In a third aspect, the invention provides a cloning vector containing a dicistronic message according to the first aspect of the present invention.

General methods by which the expression and cloning vectors may be constructed, transfection methods and culture methods are well known to those skilled in the art.

In a fourth aspect, the present invention also provides a process for the production of a particular antibody molecule comprising culturing a bacterial host cell that has been transformed with an expression vector of the present invention under conditions suitable for leading to expression of DNA encoding said antibody molecule, and isolating said antibody molecule, wherein the expression level of said antibody has been optimised.

Any suitable bacterial host cell may be used for expression of the heavy and light chains of the particular antibody molecule encoded by a dicistronic message according to the present invention. However, preferably *E. coli* host cells are used. Other microbial systems may also be used.

The antibody molecule may be secreted from the cell or targeted to the periplasm by suitable signal sequences. Alternatively, the antibody molecules may accumulate within the cell's cytoplasm. Depending on the antibody being produced and the process used, it may be desirable to allow the antibody molecule to refold and form a functional conformation. Procedures for allowing the antibody molecule to refold are well known to those skilled in the art.

The antibody molecules produced by a dicistronic message according to the present invention may be used to make a therapeutic or diagnostic composition comprising a particular antibody in combination with a pharmaceutically acceptable excipient, diluent or carrier.

The antibody molecule may be the sole active ingredient in the therapeutic or diagnostic composition or may be accompanied by one or more other active ingredients including other antibody ingredients, for example, anti-T cell, anti-IFNγ or anti-LPS antibodies, or non-antibody ingredients such as xanthines.

The particular antibody molecule produced by the present invention may be administered in any appropriate form and amount according to the therapy in which it is employed.

Suitable forms for administration include forms suitable for parenteral administration, e.g. by injection or infusion, for example, by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents.

Alternatively, the antibody molecule may be in dry form, for reconstitution before use with an appropriate sterile liquid.

If the antibody molecule is suitable for oral administration, for example in the case of antibody fragments, the formulation may contain, in addition to the active ingredient, suitable additives used in the formulation of orally administered compositions.

The therapeutic and diagnostic compositions may be in unit dosage form, in which case each unit dose comprises an effective amount of the particular antibody molecule. The dose will also be selected according to the age and condition of the patient.

If the antibody molecule has a short half life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

DETAILED DESCRIPTION OF THE INVENTION

Figure 3:
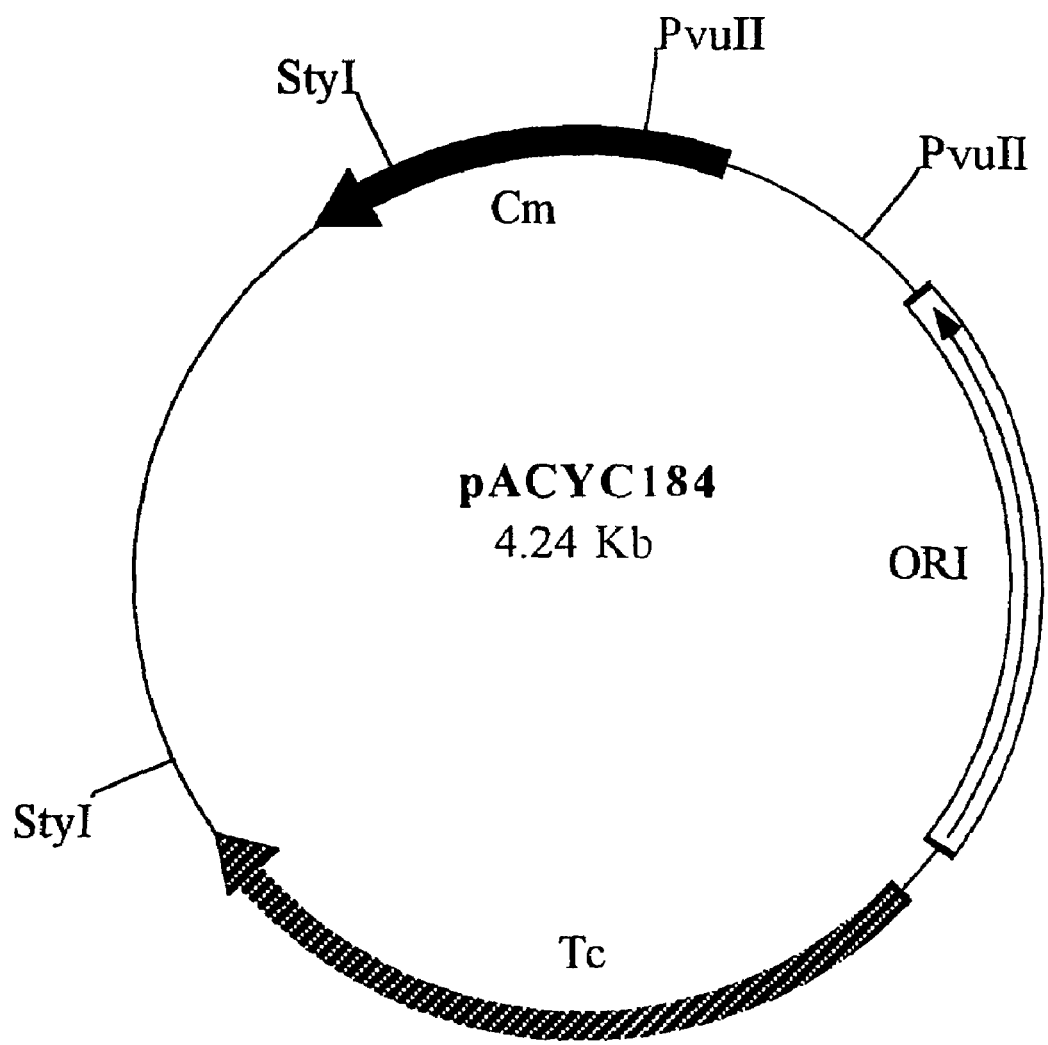
Figure 4:
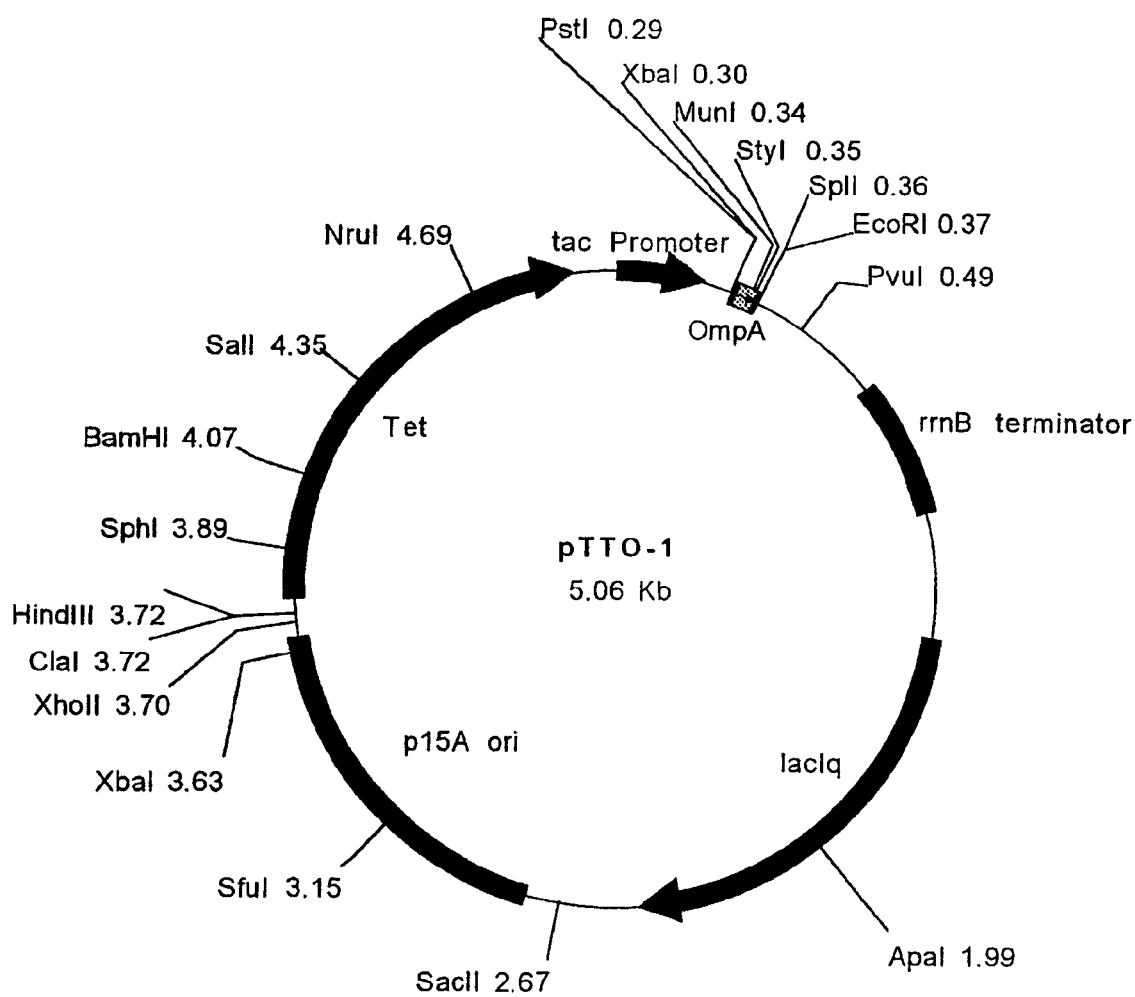
Figure 6:
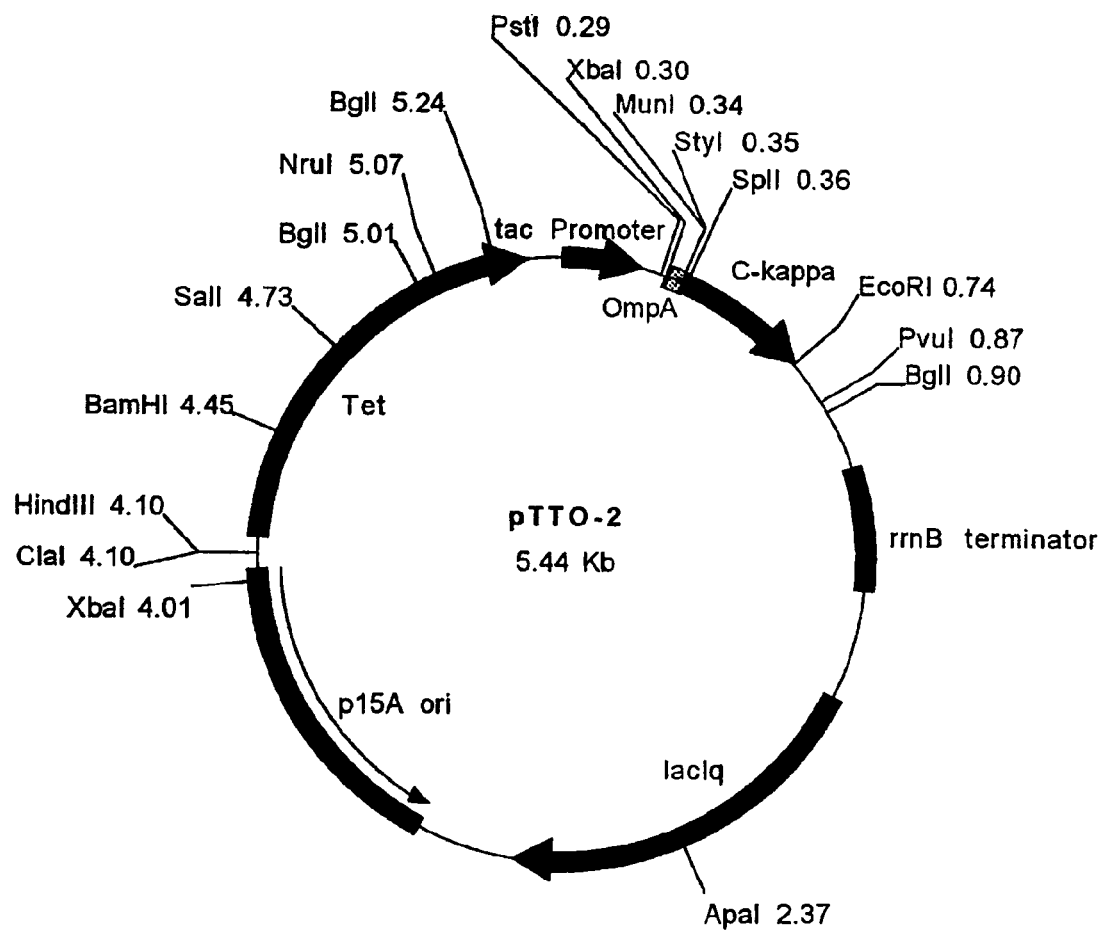
Figure 7:
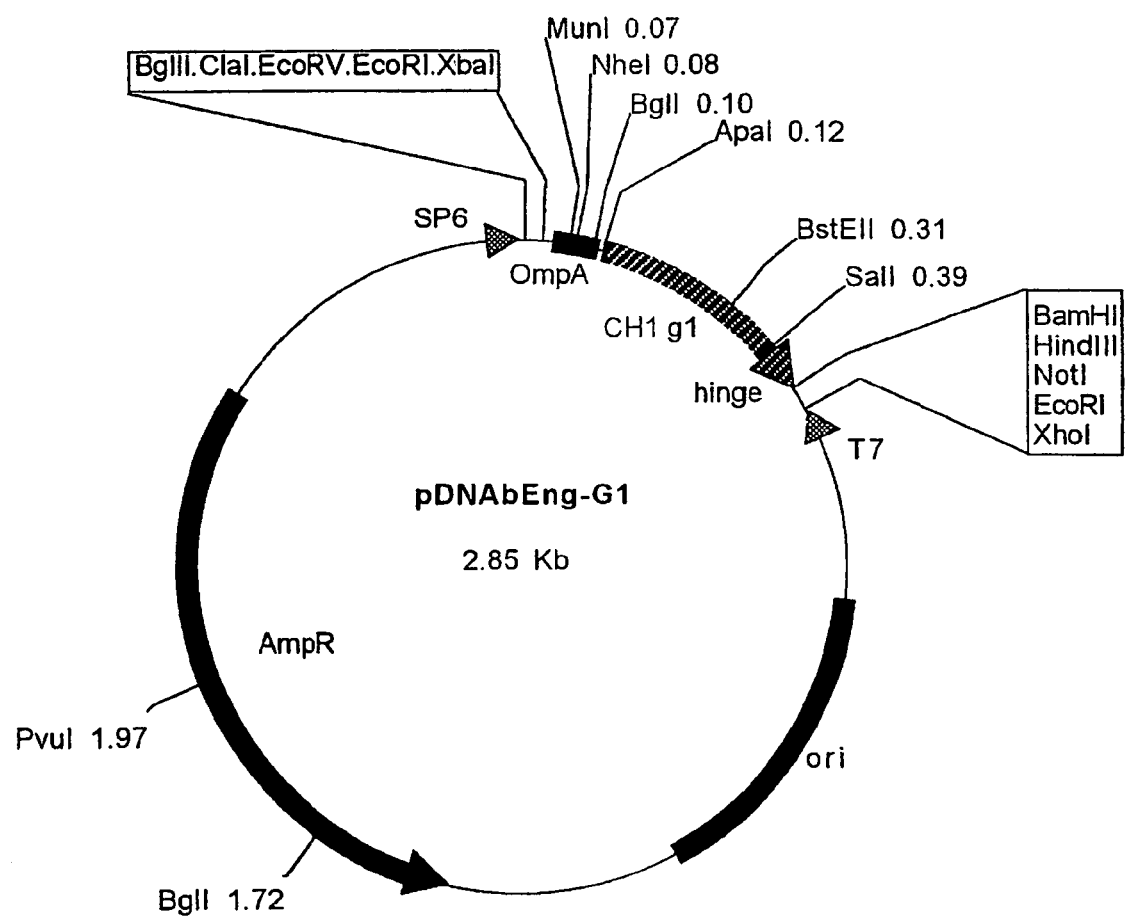
Figure 8:
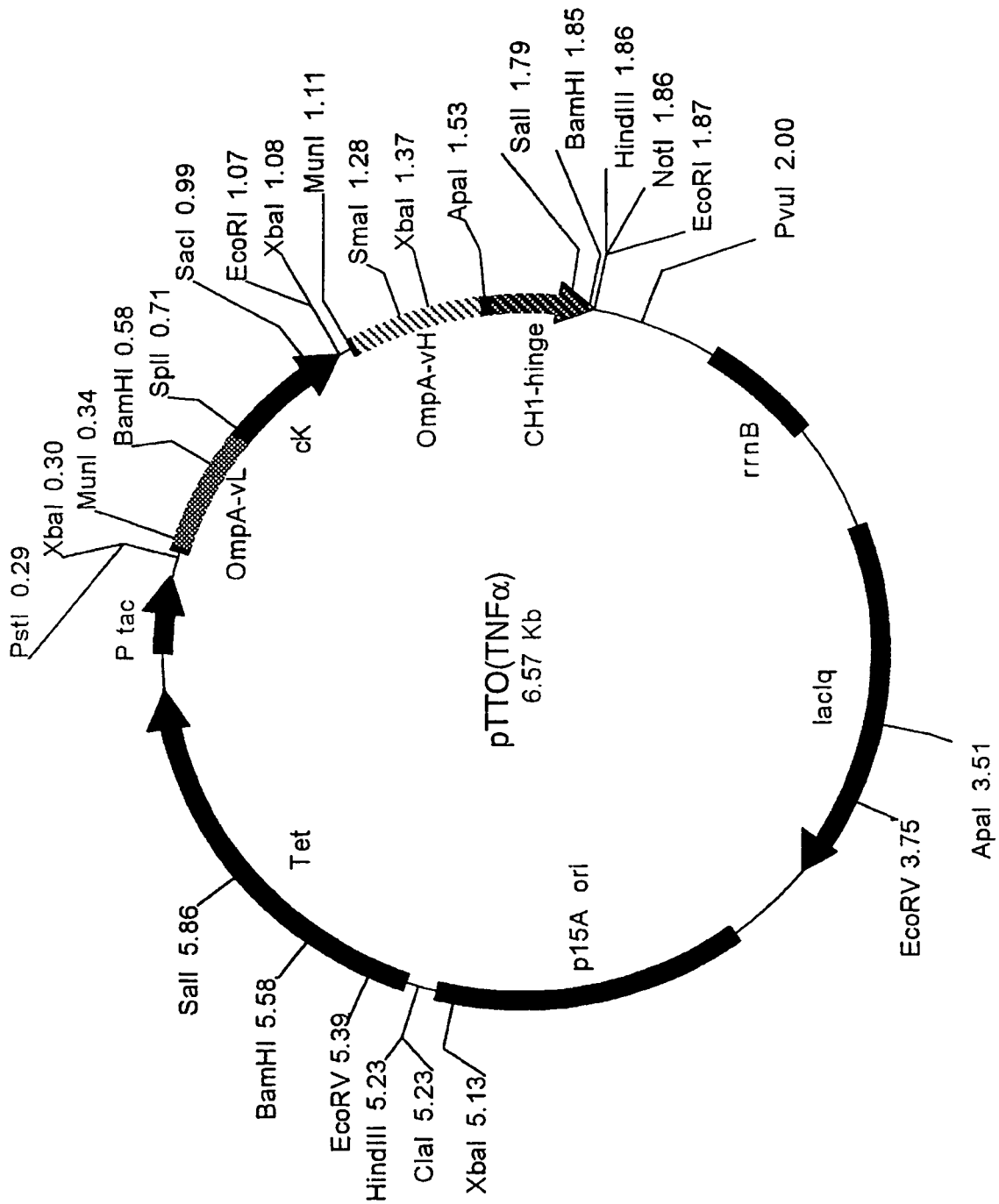
Figure 10:
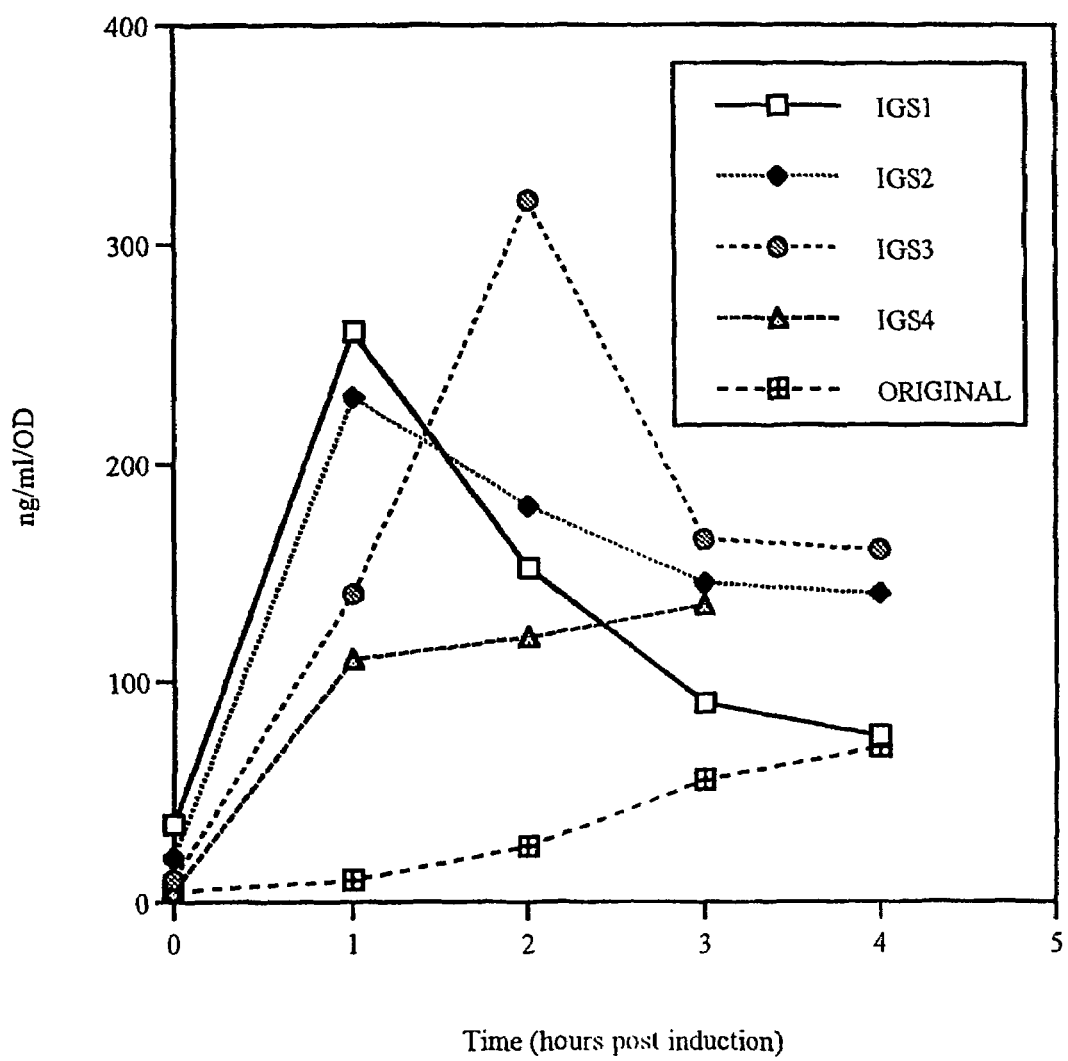
Figure 11:
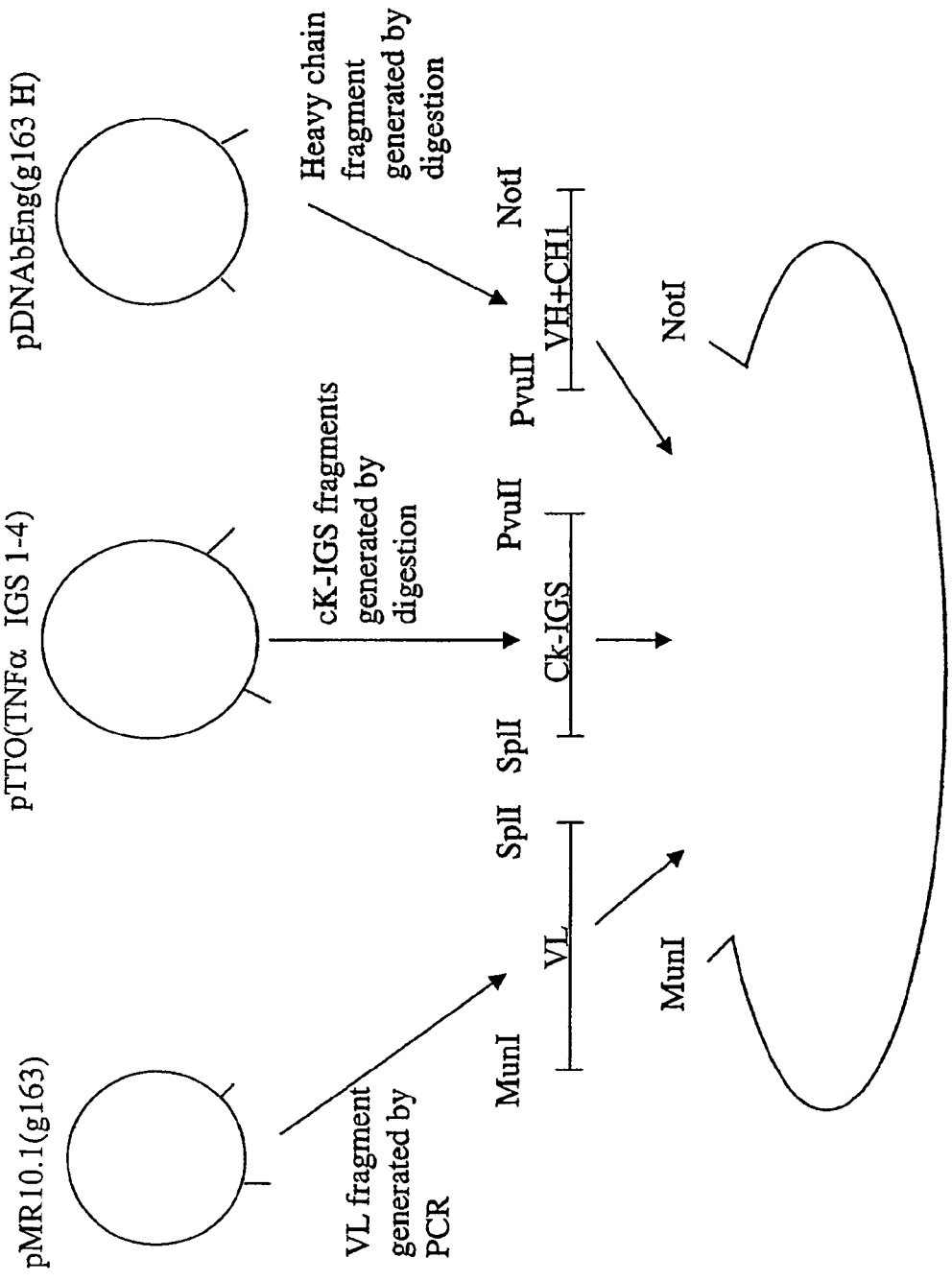
Figure 12:
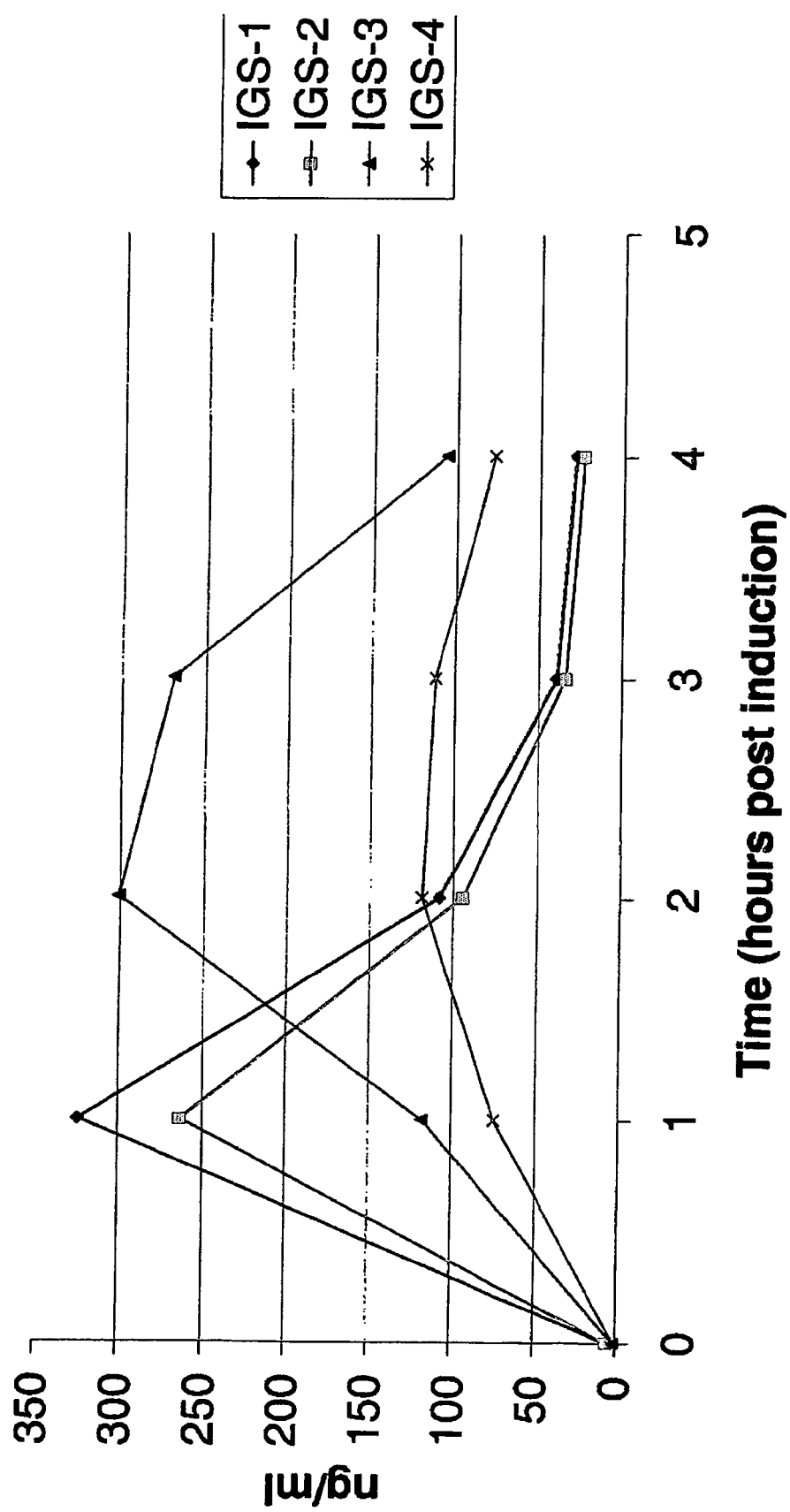
Figure 13:
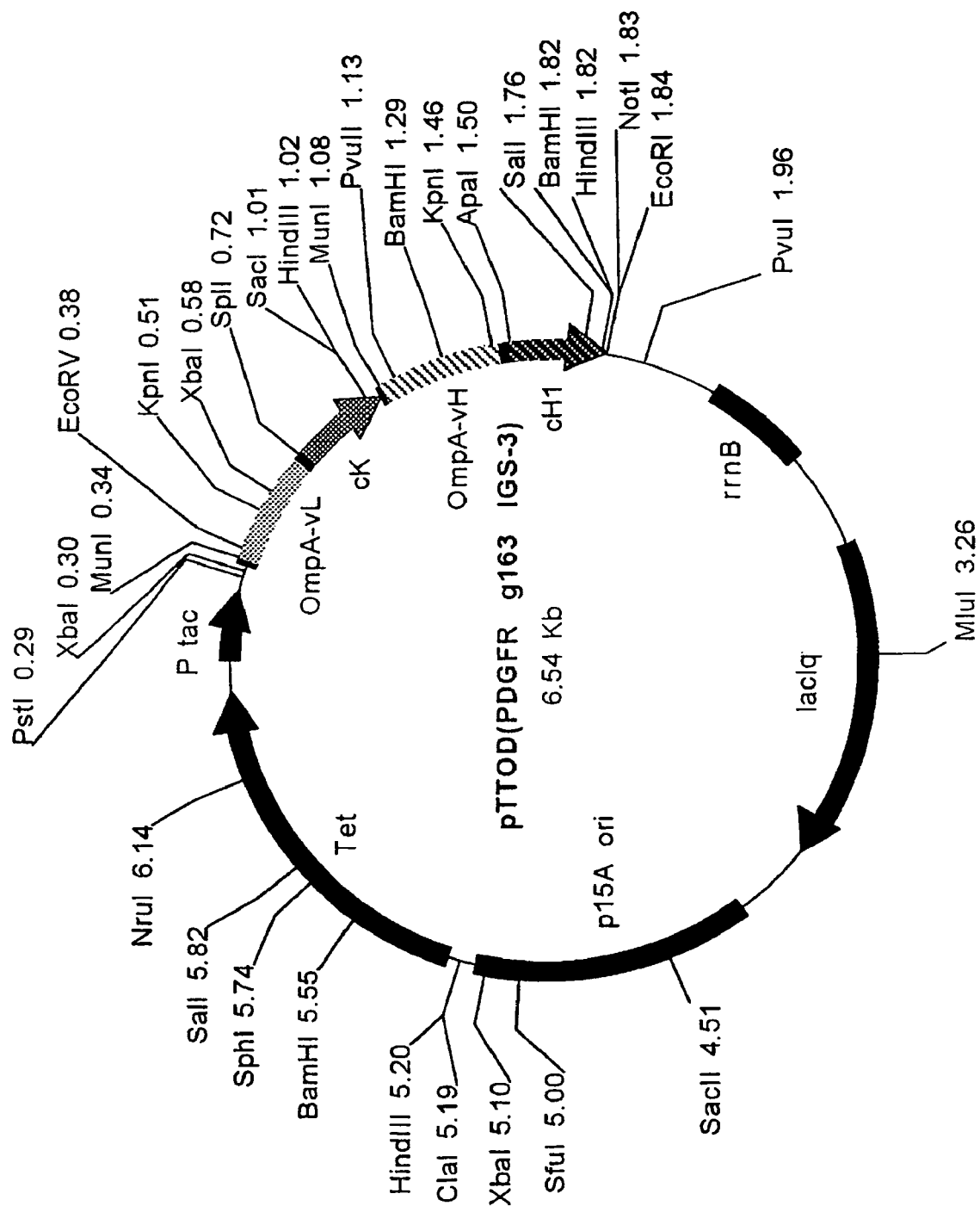
Figure 14:
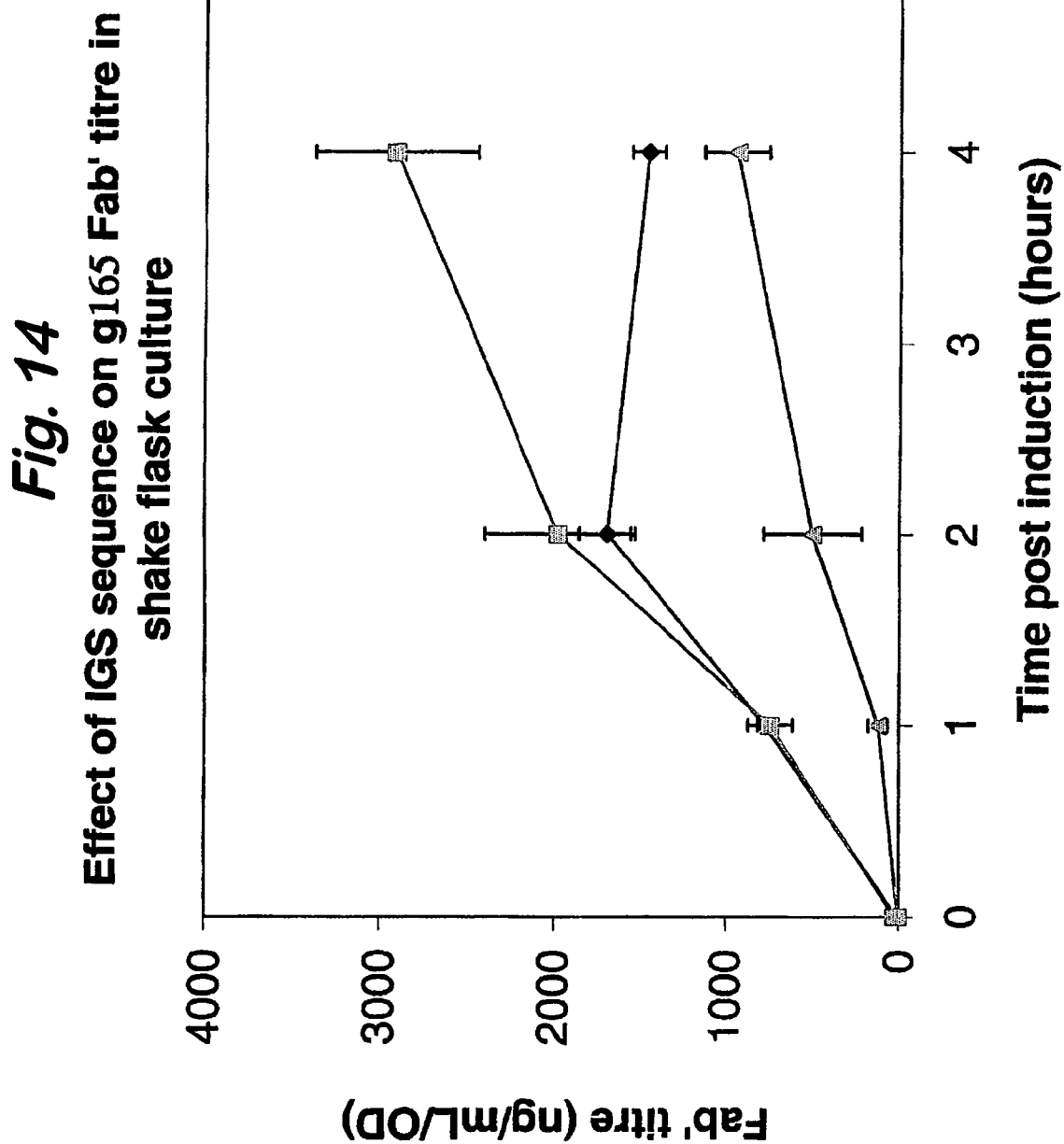
Figure 15:
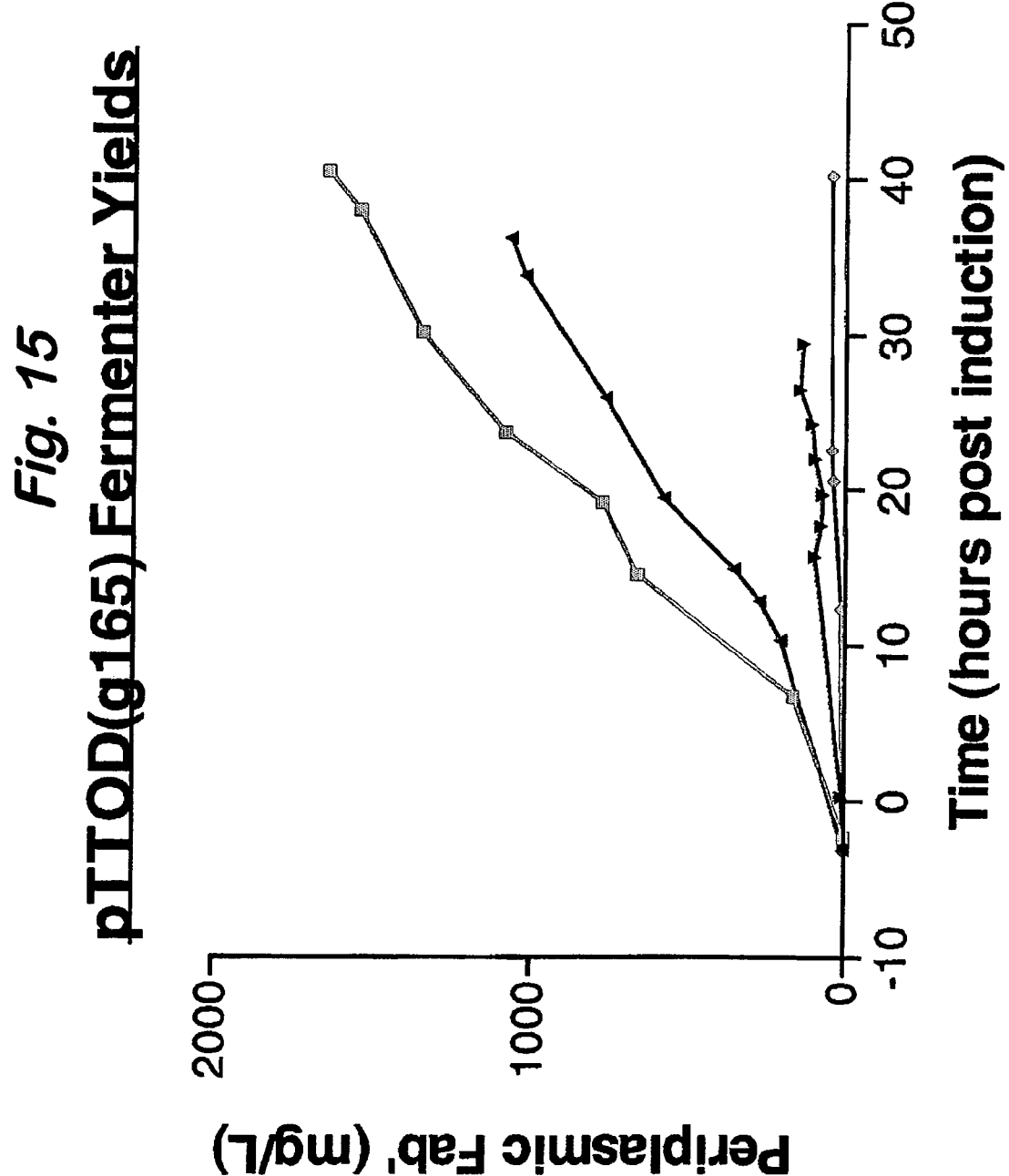
Figure 16:
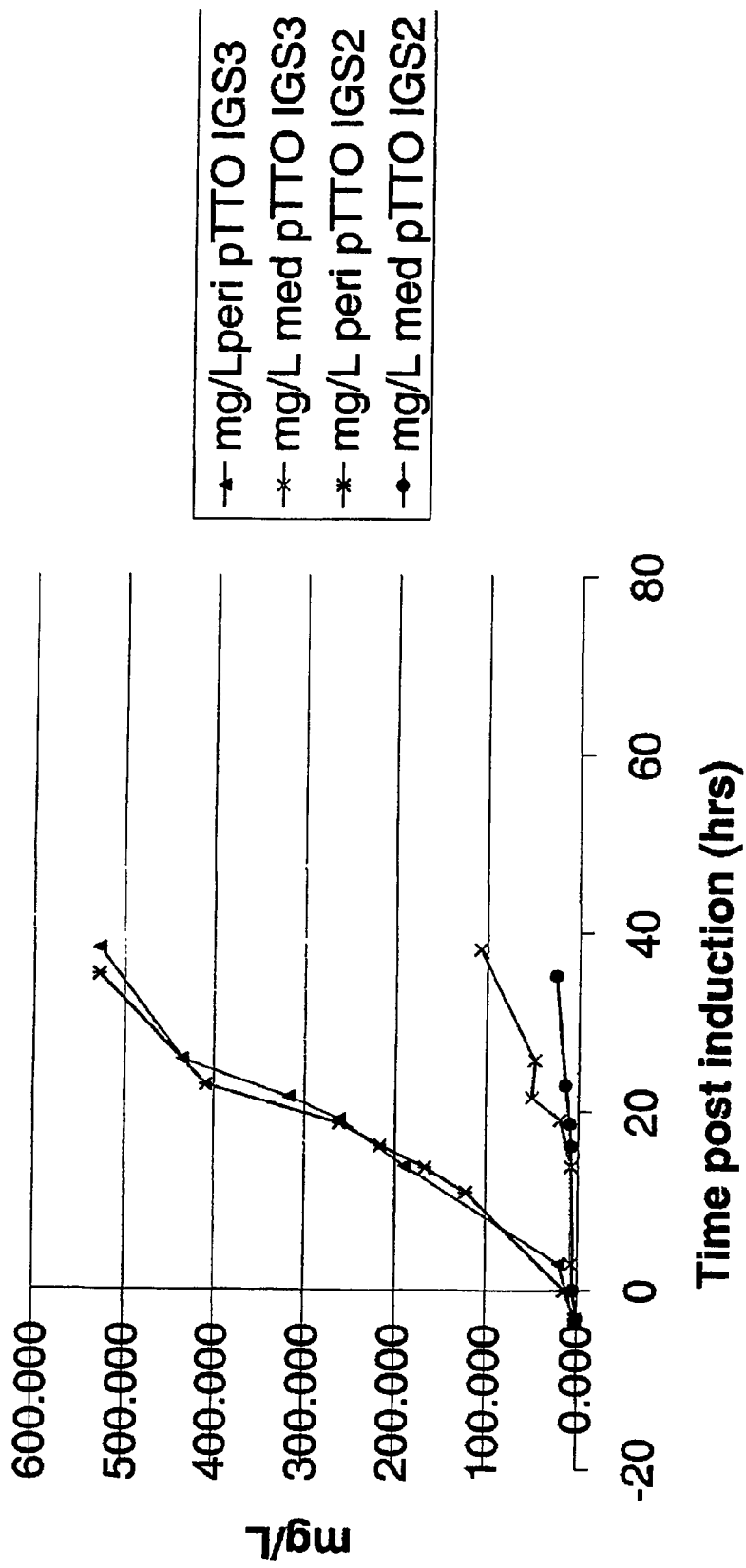

The present invention is further described by way of illustration only in the following examples which refer to the accompanying drawings in which:

FIG. 1 shows vector pTTQ9;
FIG. 2 shows the sequence of the OmpA polylinker region (SEQ ID NOs.: 1 or 2);
FIG. 3 shows vector pACYC184;
FIG. 4 shows vector pTTO-1;
FIG. 5 shows the complete DNA sequence of vector pTTO-1 (SEQ ID NO:3);
FIG. 6 shows vector pTTO-2;
FIG. 7 shows vector pDNAbEngG1;
FIG. 8 shows vector pTTO(TNFα);
FIG. 9 shows oligonucleotide cassettes encoding four different intergenic sequences for E. co/i Fab' expression (SEQ ID NOs: 4, 7, 10 and 13);
FIG. 10 shows periplasmic Fab' accumulation of IGS variants pTTO(TNFα IGS-1), pTTO(TNFα IGS-2), pTTO(TNFα IGS-3) and pTTO(TNFα IGS-4) as a result of shake-flask analysis;
FIG. 11 shows a four way ligation used to generate four IGS variants of Fab' g163;
FIG. 12 shows soluble Fab' accumulation of IGS variants pTTO(g163 IGS-1), pTTO(g163 IGS-2), pTTO(g163 IGS-3) and pTTO(g163 IGS-4) as a result of shake-flask analysis;
FIG. 13 shows a restriction map of vector pTTOD(g163 IGS-3);
FIG. 14 shows soluble Fab' accumulation of IGS variants pTTOD(g165 IGS-1), pTTOD(g165 IGS-2) and pTTOD (g165 IGS-3) as a result of shake-flask analysis;
FIG. 15 shows soluble Fab' accumulation of IGS variants pTTOD(g165 IGS-1), pTTOD(g165 IGS-2), pTTOD(g165 IGS-3) and pTTOD(g165 IGS-4) as a result of fermenter comparison analysis;
FIG. 16 shows soluble Fab' accumulation of IGS variants pTTOD(gA33 IGS-2) and pTTOD(gA33 IGS-3) as a result of fermenter comparison analysis;

EXAMPLES

A Dicistronic Message Encoding an Anti-TNFα Antibody

A dicistronic message of the present invention was used to achieve high level expression of anti-TNFα Fab' fragments. The upstream cistron encoded the light chain of the antibody whilst the downstream cistron encoded the heavy chain of the antibody. A DNA sequence encoding the OmpA signal peptide was fused to the 5' end of the DNA coding for each of the light chain and the heavy chain to allow efficient secretion to the periplasm.

A series of oligonucleotide cassettes coding for a range of different IGSs were used in the dicistronic message in order to vary the level of expression of the heavy chain. The use of different cassettes altered the rate of translational initiation of the heavy chain, resulting in a range of rates of accumulation of the translated heavy chain product.

A series of four IGSs were designed, permitting the experimental determination of the optimum sequence. The IGS variant that gave rise to the accumulation of the greatest amount of soluble Fab' was selected experimentally using shake flask expression as a guide or fermenter expression as a definitive means. Surprisingly, different IGSs were selected for different Fab's, indicating that empirical selection will be required for each new Fab' fragment to be expressed.

Experimental

Materials and Methods

General Microbiology and DNA Manipulation Techniques

*E. coli* strain INVαF' (Invitrogen, De Schelp, Netherlands) was used for transformation and routine culture growth; *E.* coli strain W3110 (ATCC # 27325) was used for expression studies. DNA restriction and modification enzymes were obtained from Boehringer Mannheim (Lewes, East Sussex, UK) and New England Biolabs (Hitchen, Herts, UK). Plasmid preparations were performed using plasmid purification kits (QIAGEN, Crawley, West Sussex, UK). DNA fragment purification was performed using QIAGEN spin columns. DNA fragments were purified from agarose using the GeneClean protocol (BIO 101). Oligonucleotides were supplied by Oswel Oligonucleotide Service and were synthesised at the 40 nM scale. PCR was performed using Perkin Elmer 'Amplitaq' as recommended. DNA sequencing reactions were performed using the ABI Prism Dye-Deoxy chain termination kit and run on an ABI 373A automated sequencer (PE Applied Biosystems, Warrington, Cheshire, UK). Data were analysed using the program AutoAssembler (PE Applied Biosystems).

A series of oligonucleotide cassettes coding for a range of different IGSs were used in the dicistronic message in order to vary the level of expression of the heavy chain. The use of different cassettes altered the rate of translational initiation of the heavy chain, resulting in a range of rates of accumulation of the translated heavy chain product.

A series of four IGSs were designed, permitting the experimental determination of the optimum sequence. The IGS variant that gave rise to the accumulation of the greatest amount of soluble Fab' was selected experimentally using shake flask expression as a guide or fermenter expression as a definitive means. Surprisingly, different IGSs were selected for different Fab's, indicating that empirical selection will be required for each new Fab' fragment to be expressed.

Experimental

Materials and Methods

General Microbiology and DNA Manipulation Techniques

*E. coli* strain INVαF' (Invitrogen, De Schelp, Netherlands) was used for transformation and routine culture growth; *E. coli* strain W3110 (ATCC # 27325) was used for expression studies. DNA restriction and modification enzymes were obtained from Boehringer Mannheim (Lewes, East Sussex, UK) and New England Biolabs (Hitchen, Herts, UK). Plasmid preparations were performed using plasmid purification kits (QIAGEN, Crawley, West Sussex, UK). DNA fragment purification was performed using QIAGEN spin columns. DNA fragments were purified from agarose using the GeneClean protocol (BIO 101). Oligonucleotides were supplied by Oswel Oligonucleotide Service and were synthesised at the 40 nM scale. PCR was performed using Perkin Elmer 'Amplitaq' as recommended. DNA sequencing reactions were performed using the ABI Prism Dye-Deoxy chain termination kit and run on an ABI 373A automated sequencer (PE Applied Biosystems, Warrington, Cheshire, UK). Data were analysed using the program AutoAssembler (PE Applied Biosystems).

Shake Flask Induction

*E. coli* W3110 cultures were grown in L-broth supplemented with tetracycline (7.5 µg/ml). For inductions, fresh overnight cultures (grown at 30° C.) were diluted to $OD_{600}$=0.1 into 200 ml L-broth in a 2 L baffled flask and were grown at 30° C. in an orbital incubator. At $OD_{600}$=0.5, IPTG was added to 200 µM. Samples (normalised for OD) were taken at intervals.

Periplasmic Extraction

Culture samples were chilled on ice (5 minutes) then cells were harvested by centrifugation. Following resuspension in extraction buffer (100 mM Tris.HCl, 10 mM EDTA; pH7.4) samples were incubated overnight at 30° C., then clarified by centrifugation.

Assembly Assay

Fab' concentrations were determined by ELISA. Plates were coated at 4° C. overnight with anti-human Fd 6045 (2 µg/ml in coating buffer, physiological saline, 100 µl per well) (see EP 491031). After washing, 100 µl of sample was loaded per well; purified A5B7 gamma-1 Fab' (see EP 491031), initially at 2 µg/ml, was used as a standard. Samples were serially diluted 2-fold across the plate in sample conjugate buffer (per litre: 6.05 g tris aminomethane; 2.92 g NaCl; 0.1 ml Tween-20; 1 ml casein (0.2%)); plates were incubated for 1 hour at room temperature, with agitation. Plates were washed and dried, then 1100 µl of anti-human C-kappa (GD12)-peroxidase was added (diluted in sample conjugate buffer). Incubation was carried out at room temperature for 1 hour with agitation. Plates were washed and dried, then 100 µl of substrate solution was added (10 ml sodium acetate/citrate solution (0.1 M, pH 6); 100 µl $H_2O_2$ solution; 100 µl tetramethyl benzidine solution (10 mg/ml in dimethylsulphoxide)). Absorbance at 630 nm was read 4-6 minutes after substrate addition.

Fermentation

*E. coli* W3110 cultures were grown in shake flasks in L-broth supplemented with tetracycline (7.5 µg/ml) at 30° C. to $OD_{600}$=1.0; 100 ml of this culture was used to inoculate 1 L of SM6 media (plus glycerol) (European Patent 651803) within a 1.5 L fed-batch culture fermenter. pH was controlled at 7.0 with 50% $NH_4OH$ and 5% $H_2SO_4$. The dissolved oxygen concentration was maintained at 30% by variable agitation. Tetracycline was not included in the fermenter medium. The initial glycerol concentration was 3% w/v; glycerol was fed on one further occasion during fermentation, such that it would cease to be available once the culture reached $OD_{600}$~60. Cultures were grown at 30° C. to $OD_{600}$=55, then 120 ml of 50% lactose was added; lactose induction follows utilisation of available glucose. A further 60 ml batch of lactose was added 20 hours later. Fermentation was monitored for 25 to 30 hours post-induction and samples (normalised for OD) were taken at intervals.

Results

Construction of Plasmids pTTO-1 and pTTO-2

Plasmid pTTQ9 was obtained from Amersham and is shown in FIG. 1. An aliquot (2 µg) was digested with restriction enzymes SalI and EcoRI, the digest was run on a 1% agarose gel and the large DNA fragment (4520 bp) was purified. Two oligonucleotides were synthesized which, when annealed together, encode the OmpA polylinker region shown in FIG. 2. This sequence has cohesive ends which are compatible with the SalI and EcoRI ends generated by restriction of pTTQ9. By cloning this oligonucleotide 'cassette' into the pTTQ9 vector, the SalI site is not regenerated, but the EcoRI site is maintained. The cassette encodes the first 13 amino acids of the signal sequence of the *E. coli* outer-membrane protein Omp-A, preceded by the Shine Dalgarno ribosome binding site of the OmpA gene. In addition restriction sites for enzymes XbaI, MunI, StyI and SplI are present. The MunI and StyI sites are within the coding region of the OmpA signal sequence and are intended as the 5' cloning sites for insertion of genes. The two oligonucleotides which make up this cassette were annealed together by mixing at a concentration of 5 pmoles/µl, heating in a waterbath to 95° C. for 3 minutes, then slow cooling to room temperature. The annealed sequence was then ligated into the SalI/EcoRI cut pTTQ9. The resulting plasmid intermediate, termed pTQOmp, was verified by DNA sequencing.

Aliquots of this intermediate were then cleaved with SspI and EcoRI (2350 bp fragment purified) and with EcoRI and XmnI (350 bp fragment purified). The 2350 bp fragment encodes the transcriptional terminator region and the lacIq gene and the 350 bp fragment encodes the tac promoter, OmpA signal sequence and multicloning site. Plasmid pACYC184 (New England Biolabs—FIG. 3) was digested with StyI, treated with Mung Bean Nuclease to generate blunt ends, then digested with PvuII (2348 bp fragment purified—this fragment encodes the tetracycline resistance marker and the p15A origin of replication). This fragment was treated with alkaline phosphatase to remove 5' terminal phosphates (to prevent self ligation) and was ligated to the other purified fragments. The resulting plasmid was termed pTTO-1 and is shown in the map in FIG. 4. FIG. 5 shows the complete DNA sequence of pTTO-1. Insertion of the human Ig light chain kappa constant domain, as a SplI-EcoRI fragment from plasmid pHC132, created pTTO-2 (FIG. 6).

Insertion of Fab' Variable Regions into pTTO-2

The variable region genes of Fab' TNFα were generated by PCR amplification from vectors for mammalian cell expression of whole antibody which contain sequence from SEQ ID8 of PCT/GB01/02477. DNA encoding the OmpA signal sequence and including the MunI restriction enzyme site for cloning in-frame into pTTO-2, was attached to the 5' end of each gene such that it replaced the native Ig leader.

The purified $V_L$ gene (MunI/SplI) was then inserted into the MunI/SplI site of pTTO-2 to create the light chain intermediate pTTO(TNFαL).

The heavy chain $V_H$ gene was cloned via the intermediate vector pDNAbEng-G1 (FIG. 7), between the MunI-ApaI sites, creating pDNAbEng(TNFαH). Cloning of the heavy chain gene from this plasmid as an EcoRI fragment into the EcoRI site of pTTO(TNFαL) created the *E. coli* expression plasmid pTTO(TNFα) (FIG. 8).

Construction of IGS Variants of pTTO(TNFα)

A series of four intergenic sequence (IGS) variants were designed (FIG. 9), permitting the empirical determination of the optimum IGS for TNFα Fab'. IGS1 and IGS2 have very short intergenic sequences (−1 and +1 respectively) and might be expected to give closely coupled translation; the SD sequences (underlined) are subtly different. These two sequences will most likely confer a high level of translational initiation. IGS3 and IGS4 have a longer distance between stop and start codons (+13) and differ in their sequence composition. The SD sequence of IGS3 is stronger than that of IGS1, 2 or 4. All sequences were studied for secondary structure (using m/fold program (Jaeger, J. A. et al. Methods Enzymology, 183: 281-306 (1990); part of GCG Wisconsin Package, Accelrys)) and 'optimised' as far as possible; however, with tight coupling of translation of the two chains the lack of ribosomal dissociation means that the mRNA may not be 'naked', preventing secondary structure formation.

The IGS variants were constructed by ligation of two fragments into a vector prepared by SacI-NotI digestion of pTTO (TNFα). An insert fragment prepared by MunI-NotI digestion of pDNAbEng(TNFα) was purified and ligated along with each IGS cassette (SacI-MunI) into the vector, creating the 4 expression plasmids pTTO(TNFαIGS-1), pTTO(TNFα IGS-2), pTTO(TNFα IGS-3) and pTTO(TNFα IGS-4).

Shake Flask Expression Analysis of TNFα IGS Variants

The four IGS variant vectors and the original expression vector pTTO(TNFα) were each used to transform *E. coli* strain W3110. The transformed *E. coli* were then analysed for Fab' expression in shake flasks as described. The results of a typical experiment are shown in FIG. 10.

The different intergenic sequences conferred different expression profiles. IGS1 and IGS2 accumulated periplasmic Fab' rapidly with a peak at 1 hour post induction, after which the level recovered fell. The peak was greater and the fall sharper for IGS1. These results were consistent with a high level of synthesis, as expected for close translational coupling for these constructs. IGS1 apparently conferred a higher level of heavy chain expression than did IGS2. In this instance, it appeared that this high level of expression was poorly tolerated, since periplasmic expression levels fell after the 1 hour peak. This was seen on the growth profile of the IGS1 culture (not shown), which peaked at 1 hour post induction before falling, suggesting cell death and lysis.

IGS3 accumulated Fab' more slowly but peaked at 2 hours post induction with a higher peak value (325 ng/ml/OD), before levels fell. The growth of this culture continued to 3 hours post induction and reached a higher peak biomass (not shown). This is consistent with a lower level of heavy chain synthesis.

IGS4 accumulated material at a slower rate still and failed to reach the high peak of productivity of the other three constructs.

All IGS variants significantly out-performed the original pTTO(TNFα) vector. The hypothesis that the different IGS sequences confer different rates of translational initiation is supported by these experimental results. For the TNFαFab' it appears that a high rate of heavy chain translational initiation is poorly tolerated and is therefore not optimal. A slower rate, as conferred by IGS3, results in better growth characteristics and consequently a better yield accumulates over time.

Following comparison of productivity in the fermenter (not shown), the IGS3 construct was selected as the highest yielding.

A Dicistronic Message Encoding a Different Fab' Antibody: Creation of 1163 Fab' IGS Variants The pTTO/IGS vector suite described above was then used for expression analysis of further Fab's. Initially, humanised Fab' g163 was used. A 4-way ligation was used to generate the 4 IGS variants of Fab' g163 (FIG. 11). A heavy chain intermediate was generated by insertion of a MunI-ApaI fragment of the g163 $V_H$ gene (obtained by PCR rescue from mammalian expression vector pGamma-4) into plasmid pDNAbEngG1. This intermediate was cleaved with PvuII and NotI to generate a g163 $V_H$+$C_H1$ fragment. The plasmid pTTO (TNFα) was cleaved with MunI and NotI and the large fragment was purified to give a vector fragment. A MunI-SplI $V_L$ fragment was generated by PCR rescue from the mammalian expression vector pMR10.1 (g163). Finally CK-IGS fragments were generated by SplI-PvuII digestion of the 4 pTTO (TNFα) IGS variants described above. Four separate ligations then generated the constructs pTTO(g163 IGS-1), pTTO(g163 IGS-2), pTTO(g163 IGS-3) and pTTO(g163 IGS-4). The results of shake flask analysis of these constructs are shown in FIG. 12.

The expression profile was quite similar to that seen with Fab' TNFα, in that IGS-1 and -2 resulted in very rapid Fab' accumulation, peaking at 1 hour post induction before reducing sharply. IGS-3 resulted in a slower initial rate of accumulation, peaking at a later time point (2-3 hours post induction) before reducing at a slower rate. The IGS-4 construct rose slowly throughout the induction timecourse and again never reached the high yields of the other constructs. Because of the expression profiles, and the growth profiles showing that, for IGS-1 and -2, the biomass also peaked only 1 hour post induction (not shown), IGS-3 was chosen and expressed in the fermenter to high yields (not shown).

Construction of Plasmid pTTOD

In order to simplify Fab' coding strategies, plasmid pTTOD was derived from plasmid pTTO-1 by removal of backbone restriction sites for PvuII (3 sites), EcoRV (2 sites) and ApaI (1 site). In making these changes, the protein coding sequences of the lacIq gene and tetracycline resistance gene were not altered, although 'silent' changes were made at the DNA level. A PCR strategy was used, in which primers bearing 'silent' changes, which removed these restriction sites, were designed and used to amplify sections of the parent plasmid (pTTO-1). Flanking restriction sites (unaltered) were then used to replace sequences in the parent plasmid with these modified sequences. Plasmid pTTOD was created by this multi-stage process. Transfer of existing g163 Fab' genes within vector pTTO into pTTOD was achieved using the unique PstI and EcoRI sites which flank the genes, creating pTTOD(g163) IGS variants 1-4. FIG. 13 shows the restriction map of pTTOD(g163 IGS-3).

Expression of Other Fab's as IGS Variants

In addition to TNFα and g163, several more Fab's have been expressed as two or more IGS variants. These include Fab's termed g165 and gA33. FIG. 14 shows pTTOD(g165) IGS-1 to −3 compared in the shake flask. In contrast to TNFα and g163, IGS-2 and IGS-1 out-perform IGS-3. Expression of this Fab' seems to be well tolerated by the host cell even at a rapid rate, and the culture expressing IGS-2 continued to grow throughout the induction period (not shown). FIG. 15 shows a fermenter comparison of IGS-1 to 4 with this Fab', and this essentially reproduces the observation made in the shake flask. IGS-2 was confirmed as the highest yielding variant. With Fab' gA33, pTTOD(gA33) IGS-2 and -3 were compared in the fermenter and both gave similar yields (FIG. 16). Hence, with different Fab's, different IGS sequences are required for optimum yield.

Shake Flask Versus Fermenter Analysis

In the shake flask, promoter de-repression is achieved with IPTG which gives very rapid induction of expression. The induction regime in the fermenter is different and more gentle, using lactose (which is converted by the bacterium to allolactose) to switch on the promoter. Despite these different induction kinetics, the shake flask has been shown to give an indication of how constructs will compare in the fermenter (see FIGS. 14 and 15).

The principle that different Fab's require a different IGS for optimum yield is clearly demonstrated. The novelty of the system described here is in the use of IGS cassettes to achieve optimal translational initiation rates of the second gene of a dicistronic message as a means of achieving high level Fab' expression. In the system described, the light chain expression remains unaltered and only the heavy chain translational initiation rate is optimised. There are two possible explanations for why this strategy succeeds:

(i) The expression of the light chain is of little consequence to the overall level of Fab' accumulation, provided sufficient light chain is synthesised to prevent the heavy chain becoming in excess. Excess light chain is usually tolerated without problem, and it is the level of translation of the heavy chain that dictates the efficiency of soluble expression; or (ii) The optimisation of heavy chain in effect is tuned for the fixed rate of light chain expression, so that the levels of the two chains are balanced. It is not the heavy chain folding/secretion rate per se that dictates the efficiency of soluble expression, but the balance of expression of the two heterologous chains.

It should be understood that the above described examples are merely exemplary and do not limit the scope of the present invention as defined in the following claims.

What is claimed is:

1. A nucleic acid comprising a dicistronic message for producing an antibody molecule with a particular antigen-binding specificity, in which the upstream cistron contains DNA coding for either the heavy chain or the light chain of the antibody and the downstream cistron contains DNA coding for the corresponding light chain or heavy chain respectively, characterized in that the two cistrons are linked by an intergenic sequence (IGS), wherein the IGS is IGS1 (SEQ ID NO:4), IGS2 (SEQ ID NO:7), IGS3 (SEQ ID NO:10) or IGS4 (SEQ ID NO:13), and wherein the antibody produced is not an anti-TNFα antibody or an anti-human kinase insert domain-containing receptor antibody.

2. An expression vector containing a nucleic acid according to claim 1.

3. An expression vector according to claim 2, wherein the expression vector is pTTO-1.

4. A host cell that has been transformed with an expression vector according to claim 2.

5. A host cell according to claim 4, wherein the host cell is *E. coli*.

6. A process for the production of an antibody molecule comprising culturing the host cell of claim 4.

* * * * *

SEQUENCE LISTING

<160> NUMBER OF SEQ ID NOS: 16

<210> SEQ ID NO 1
<211> LENGTH: 84
<212> TYPE: DNA
<213> ORGANISM: Artificial Sequence
<220> FEATURE:
<223> OTHER INFORMATION: OmpA oligonucleotide adaptor

<400> SEQUENCE: 1
tcgagttcta gataacgagg cgtaaaaaat gaaaaagaca gctatcgcaa ttgcagtggc        60
cttggctctg acgtacgagt cagg        84

<210> SEQ ID NO 2
<211> LENGTH: 13
<212> TYPE: PRT
<213> ORGANISM: Artificial Sequence
<220> FEATURE:
<223> OTHER INFORMATION: OmpA oligonucleotide adaptor

<400> SEQUENCE: 2

Met Lys Lys Thr Ala Ile Ala Ile Ala Val Ala Leu Ala
1               5                   10

```
<210> SEQ ID NO 3
<211> LENGTH: 5077
<212> TYPE: DNA
<213> ORGANISM: Artificial Sequence
<220> FEATURE:
<223> OTHER INFORMATION: pTTO-1 expresson vector

<400> SEQUENCE: 3
aattctcatg tttgacagct tatcatcgac tgcacggtgc accaatgctt ctggcgtcag      60
gcagccatcg gaagctgtgg tatggctgtg caggtcgtaa atcactgcat aattcgtgtc     120
gctcaaggcg cactcccgtt ctggataatg ttttttgcgc cgacatcata acggttctgg     180
caaatattct gaaatgagct gttgacaatt aatcatcggc tcgtataatg tgtggaattg     240
tgagcggata acaatttcac acaggaaaca gcgatgagct ggctgcagg tcgagttcta      300 gataacgagg cgtaaaaaat gaaaagaca gctatcgcaa ttgcagtggc cttggctctg     360
acgtacgagt caggaattca ctggccgtcg ttttacaacg tcgtgactgg gaaaaccctg     420
gcgttaccca acttaatcgc cttgcagcac atccccctttt cgccagctgg cgtaatagcg     480
aagaggcccg caccgatcgc ccttcccaac agttgcgcag cctgaatggc gaatggcgcc     540
tgatgcggta ttttctcctt acgcatctgt gcggtatttc acaccgcata aattccctgt     600 tttgcggat gagagaagat tttcagcctg atacagatta aatcagaacg cagaagcggt      660
ctgataaaac agaatttgcc tggcggcagt agcgcggtgg tcccacctga ccccatgccg     720
aactcagaag tgaaacgccg tagcgccgat ggtagtgtgg ggtctcccca tgcgagagta     780
gggaactgcc aggcatcaaa taaaacgaaa ggctcagtcg aaagactggg cctttcgttt     840
tatctgttgt ttgtcggtga acgctctcct gagtaggaca atccgccgg gagcggattt      900 gaacgttgcg aagcaacggc ccggagggtg gcgggcagga cgcccgccat aaactgccag     960
gcatcaaatt aagcagaagg ccatcctgac ggatggcctt tttgcgtttc tacaaactct    1020
tcctgtcgtc atatctacaa gccatccccc cacagatacg gtaaactagc ctcgtttttg    1080
catcaggaaa gcagggaatt tatggtgcac tctcagtaca atctgctctg atgccgcata    1140
gttaagccag ccccgacacc cgccaacacc cgctgacgcg ccctgacggg cttgtctgct    1200
cccggcatcc gcttacagac aagctgtgac cgtctccggg agctgcatgt gtcagaggtt    1260
ttcaccgtca tcaccgaaac gcgcgagacg aaagggcctc gtgatacgcc tatttttata    1320
ggttaatgtc atgataataa tggtttctta cgtgaggt tctgtacccg acaccatcga      1380
atggtgcaaa acctttcgcg gtatggcatg atagcgcccg aagagagtc aattcagggt     1440 ggtgaatgtg aaaccagtaa cgttatacga gcgaaaacgc gggaaaaagt ggaagcggcg    1500
atggcggagc tgaattacat tcccaaccgc gtggcacaac aactggcggg caaacagtcg    1560
ttgctgattg gcgttgccac ctccagtctg gccctgcacg cgccgtcgca aattgtcgcg    1620
gcgattaaat ctcgcgccga tcaactgggt gccagcgtgg tggtgtcgat ggtagaacga    1680
agcggcgtcg aagcctgtaa agcggcggtg cacaatcttc tcgcgcaacg cgtcagtggg    1740
ctgatcatta actatccgct ggatgaccag gatgccattg ctgtggaagc tgcctgcact    1800
aatgttccgg cgttatttct tgatgtctct gaccagacac ccatcaacag tattattttc    1860
tcccatgaag acggtacgcg actgggcgtg gagcatctgg tcgcattggg tcaccagcaa    1920
atcgcgctgt tagcgggccc attaagttct gtctcggcgc gtctgcgtct ggctggctgg    1980
cataaatatc tcactcgcaa tcaaattcag ccgatagcgg aacggaagg cgactggagt     2040 gccatgtccg gttttcaaca aaccatgcaa atgctgaatg agggcatcgt tcccactgcg    2100
```

```
atgctggttg ccaacgatca gatggcgctg ggcgcaatgc gcgccattac cgagtccggg    2160
ctgcgcgttg gtgcggatat ctcggtagtg ggatacgacg ataccgaaga cagctcatgt    2220
tatatcccgc cgttaaccac catcaaacag gattttcgcc tgctggggca aaccagcgtg    2280
gaccgcttgc tgcaactctc tcagggccag gcggtgaagg gcaatcagct gttgcccgtc    2340
tcactggtga aaagaaaaac caccctggcg cccaatacgc aaaccgcctc tccccgcgcg    2400
ttggccgatt cattaatgca gctggcacga caggtttccc gactggaaag cgcttccgac    2460
ctgcaagaac ctcacgtcag gtggcacttt cggggaaat gtgcgcggaa ccctatttg    2520 tgggcagtga gcgcaacgca attaatgtaa gttagctcac tcattaggca ccccaggctt    2580
tacactttat gcttccgacc tgcaagaacc tcacgtcagg tggcacttttt cggggaaatg    2640 tgcgcggaac ccctatttgt ttatttttct aaatacattc aaatatgtat ccgctcatga    2700
gacaataacc ctgataaatg cttcaataat ctgtccctcc tgttcagcta ctgacggggt    2760
ggtgcgtaac ggcaaaagca ccgccggaca tcagcgctag cggagtgtat actggcttac    2820
tatgttggca ctgatgaggg tgtcagtgaa gtgcttcatg tggcaggaga aaaaaggctg    2880
caccggtgcg tcagcagaat atgtgataca ggatatattc cgcttcctcg ctcactgact    2940
cgctacgctc ggtcgttcga ctgcggcgag cggaaatggc ttacgaacgg ggcggagatt    3000
tcctggaaga tgccaggaag atacttaaca gggaagtgag agggccgcgg caaagccgtt    3060
tttccatagg ctccgccccc ctgacaagca tcacgaaatc tgacgctcaa atcagtggtg    3120
gcgaaacccg acaggactat aaagatacca ggcgtttccc cctggcggct ccctcgtgcg    3180
ctctcctgtt cctgcctttc ggtttaccgg tgtcattccg ctgttatggc cgcgtttgtc    3240
tcattccacg cctgacactc agttccgggt aggcagttcg ctccaagctg gactgtatgc    3300
acgaaccccc cgttcagtcc gaccgctgcg ccttatccgg taactatcgt cttgagtcca    3360
acccggaaag acatgcaaaa gcaccactgg cagcagccac tggtaattga tttagaggag    3420
ttagtcttga agtcatgcgc cggttaaggc taaactgaaa ggacaagttt tggtgactgc    3480
gctcctccaa gccagttacc tcggttcaaa gagttggtag ctcagagaac cttcgaaaaa    3540
ccgccctgca aggcggtttt tcgtttttca gagcaagaga ttacgcgcag accaaaacga    3600
tctcaagaag atcatcttat taatcagata aaatatttct agatttcagt gcaatttatc    3660
tcttcaaatg tagcacctga agtcagcccc atacgatata agttgtaatt ctcatgtttg    3720
acagcttatc atcgataagc tttaatgcgg tagtttatca cagttaaatt gctaacgcag    3780
tcaggcaccg tgtatgaaat ctaacaatgc gctcatcgtc atcctcggca ccgtcaccct    3840
ggatgctgta ggcataggct tggttatgcc ggtactgccg gcctcttgc gggatatcgt    3900 ccattccgac agcatcgcca gtcactatgg cgtgctgcta gcgctatatg cgttgatgca    3960
atttctatgc gcacccgttc tcggagcact gtccgaccgc tttggccgcc gcccagtcct    4020
gctcgcttcg ctacttggag ccactatcga ctacgcgatc atggcgacca cacccgtcct    4080
gtggatcctc tacgccggac gcatcgtggc cggcatcacc ggcgccacag gtgcggttgc    4140
tggcgcctat atcgccgaca tcaccgatgg ggaagatcgg gctcgccact tcgggctcat    4200
gagcgcttgt ttcggcgtgg gtatggtggc aggccccgtg gccggggac tgttgggcgc    4260 catctccttg catgcaccat tccttgcggc ggcggtgctc aacggcctca acctactact    4320
gggctgcttc ctaatgcagg agtcgcataa gggagagcgt cgaccgatgc ccttgagagc    4380
cttcaaccca gtcagctcct tccggtgggc gcggggcatg actatcgtcg ccgcacttat    4440
gactgtcttc tttatcatgc aactcgtagg acaggtgccg gcagcgctct gggtcatttt    4500
```

-continued

```
cggcgaggac cgctttcgct ggagcgcgac gatgatcggc ctgtcgcttg cggtattcgg      4560
aatcttgcac gccctcgctc aagccttcgt cactggtccc gccaccaaac gtttcggcga      4620
gaagcaggcc attatcgccg gcatggcggc cgacgcgctg ggctacgtct tgctggcgtt      4680
cgcgacgcga ggctggatgg ccttccccat tatgattctt ctcgcttccg gcggcatcgg      4740
gatgcccgcg ttgcaggcca tgctgtccag gcaggtagat gacgaccatc agggacagct      4800
tcaaggatcg ctcgcggctc ttaccagcct aacttcgatc attggaccgc tgatcgtcac      4860
ggcgatttat gccgcctcgg cgagcacatg gaacgggttg gcatggattg taggcgccgc      4920
cctataccct tgtctgcctcc ccgcgttgcg tcgcggtgca tggagccggg ccacctcgac      4980
ctgaatggaa gccggcggca cctcgctaac ggattcacca ctccaagaat tggagccaat      5040
caattcttgc ggagaactgt gaatgcgcaa accaacc                                5077
```

<210> SEQ ID NO 4
<211> LENGTH: 67
<212> TYPE: DNA
<213> ORGANISM: Artificial Sequence
<220> FEATURE:
<223> OTHER INFORMATION: IGS Cassette-1

<400> SEQUENCE: 4

```
gagctcacca gtaacaaaaa gttttaatag aggagagtgt taatgaagaa gactgctata      60
gcaattg                                                                 67
```

<210> SEQ ID NO 5
<211> LENGTH: 13
<212> TYPE: PRT
<213> ORGANISM: Artificial Sequence
<220> FEATURE:
<223> OTHER INFORMATION: IGS Cassette-1
<220> FEATURE:
<223> OTHER INFORMATION: End of c-Kappa sequence

<400> SEQUENCE: 5

```
Ser Ser Pro Val Thr Lys Ser Phe Asn Arg Gly Glu Cys
1               5                   10
```

<210> SEQ ID NO 6
<211> LENGTH: 8
<212> TYPE: PRT
<213> ORGANISM: Artificial Sequence
<220> FEATURE:
<223> OTHER INFORMATION: IGS Cassette-1
<220> FEATURE:
<223> OTHER INFORMATION: Start of OmpA sequence

<400> SEQUENCE: 6

```
Met Lys Lys Thr Ala Ile Ala Ile
1               5
```

<210> SEQ ID NO 7
<211> LENGTH: 69
<212> TYPE: DNA
<213> ORGANISM: Artificial Sequence
<220> FEATURE:
<223> OTHER INFORMATION: IGS Cassette-2

<400> SEQUENCE: 7

```
gagctcacca gtaacaaaaa gttttaatag aggggagtgt taaaatgaag aagactgcta      60
tagcaattg                                                               69
```

```
<210> SEQ ID NO 8
<211> LENGTH: 13
<212> TYPE: PRT
<213> ORGANISM: Artificial Sequence
<220> FEATURE:
<223> OTHER INFORMATION: IGS Cassette-2
<220> FEATURE:
<223> OTHER INFORMATION: End of c-Kappa sequence

<400> SEQUENCE: 8

Ser Ser Pro Val Thr Lys Ser Phe Asn Arg Gly Glu Cys
1               5                   10

<210> SEQ ID NO 9
<211> LENGTH: 8
<212> TYPE: PRT
<213> ORGANISM: Artificial Sequence
<220> FEATURE:
<223> OTHER INFORMATION: IGS Cassette-2
<220> FEATURE:
<223> OTHER INFORMATION: Start of OmpA sequence

<400> SEQUENCE: 9

Met Lys Lys Thr Ala Ile Ala Ile
1               5

<210> SEQ ID NO 10
<211> LENGTH: 81
<212> TYPE: DNA
<213> ORGANISM: Artificial Sequence
<220> FEATURE:
<223> OTHER INFORMATION: IGS cassette-3

<400> SEQUENCE: 10
gagctcacca gtaacaaaaa gctttaatag aggagagtgt tgaggaggaa aaaaaaatga      60
agaaaactgc tatagcaatt g                                                81

<210> SEQ ID NO 11
<211> LENGTH: 13
<212> TYPE: PRT
<213> ORGANISM: Artificial Sequence
<220> FEATURE:
<223> OTHER INFORMATION: IGS cassette-3
<220> FEATURE:
<223> OTHER INFORMATION: End of c-Kappa sequence

<400> SEQUENCE: 11

Ser Ser Pro Val Thr Lys Ser Phe Asn Arg Gly Glu Cys
1               5                   10

<210> SEQ ID NO 12
<211> LENGTH: 7
<212> TYPE: PRT
<213> ORGANISM: Artificial Sequence
<220> FEATURE:
<223> OTHER INFORMATION: IGS cassette-3
<220> FEATURE:
<223> OTHER INFORMATION: Start of OmpA sequence

<400> SEQUENCE: 12

Met Lys Lys Thr Ala Ile Ala
1               5

<210> SEQ ID NO 13
<211> LENGTH: 81
<212> TYPE: DNA
<213> ORGANISM: Artificial Sequence
```

```
<220> FEATURE:
<223> OTHER INFORMATION: IGS cassette-4

<400> SEQUENCE: 13
gagctcacca gtaacaaaaa gttttaatag aggagagtgt tgacgaggat tatataatga      60
agaaaactgc tatagcaatt g                                               81

<210> SEQ ID NO 14
<211> LENGTH: 13
<212> TYPE: PRT
<213> ORGANISM: Artificial Sequence
<220> FEATURE:
<223> OTHER INFORMATION: IGS cassette-4
<220> FEATURE:
<223> OTHER INFORMATION: End of c-Kappa sequence

<400> SEQUENCE: 14

Ser Ser Pro Val Thr Lys Ser Phe Asn Arg Gly Glu Cys
1               5                   10

<210> SEQ ID NO 15
<211> LENGTH: 8
<212> TYPE: PRT
<213> ORGANISM: Artificial Sequence
<220> FEATURE:
<223> OTHER INFORMATION: IGS cassette-4
<220> FEATURE:
<223> OTHER INFORMATION: Start of OmpA sequence

<400> SEQUENCE: 15

Met Lys Lys Thr Ala Ile Ala Ile
1               5

<210> SEQ ID NO 16
<211> LENGTH: 84
<212> TYPE: DNA
<213> ORGANISM: Artificial Sequence
<220> FEATURE:
<223> OTHER INFORMATION: OmpA Oligonucleotide Adapter

<400> SEQUENCE: 16
caagatctat tgctccgcat tttttacttt ttctgtcgat agcgttaacg tcaccggaac      60
cgagactgca tgctcagtcc ttaa                                            84
```